United States Patent
Kuroda et al.

(10) Patent No.: US 9,587,219 B2
(45) Date of Patent: Mar. 7, 2017

(54) METHOD FOR PRODUCING CELL CULTURE VESSEL

(71) Applicant: Dai Nippon Printing Co., Ltd., Tokyo (JP)

(72) Inventors: Masatoshi Kuroda, Tokyo (JP); Katsunori Tsuchiya, Tokyo (JP); Masahiko Hase, Tokyo (JP); Taro Nagai, Tokyo (JP); Yumiko Narita, Tokyo (JP); Kazumasa Yamaki, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 372 days.

(21) Appl. No.: 14/357,002

(22) PCT Filed: Oct. 29, 2012

(86) PCT No.: PCT/JP2012/077843
§ 371 (c)(1),
(2) Date: May 8, 2014

(87) PCT Pub. No.: WO2013/069490
PCT Pub. Date: May 16, 2013

(65) Prior Publication Data
US 2014/0326391 A1    Nov. 6, 2014

(30) Foreign Application Priority Data
Nov. 8, 2011   (JP) .................................. 2011-244719

(51) Int. Cl.
*C12N 5/00*   (2006.01)
*B29C 65/00*  (2006.01)
(Continued)

(52) U.S. Cl.
CPC ........... *C12N 5/0602* (2013.01); *C12M 23/08* (2013.01); *C12M 23/20* (2013.01); *Y10T 156/1062* (2015.01)

(58) Field of Classification Search
CPC ... C12N 5/00; C12N 5/06; C12N 5/06; C12N 5/0602; C12M 23/00; C12M 23/08;
(Continued)

(56) References Cited

U.S. PATENT DOCUMENTS

| 5,284,766 A | 2/1994 | Okano et al. |
| 2008/0227203 A1 | 9/2008 | Watanabe et al. |
| 2009/0246872 A1 | 10/2009 | Ozawa et al. |
| 2009/0298164 A1 | 12/2009 | Cattadoris et al. |
| 2011/0097802 A1 | 4/2011 | Takada et al. |

FOREIGN PATENT DOCUMENTS

| JP | 61104974 | 5/1986 |
| JP | 2-211865 | 8/1990 |

(Continued)

OTHER PUBLICATIONS

International Search Report of International Application No. PCT/JP2012/077843, Mailed Dec. 18, 2012, 2 Pages.

*Primary Examiner* — Michael N Orlando
*Assistant Examiner* — Matthew Hoover
(74) *Attorney, Agent, or Firm* — McCarter & English, LLP

(57) ABSTRACT

This invention provides a cost-effective technique for mass-production of a cell culture vessel that allows mass cell culture to be performed in a manner that allows cells to be stably detached from the culture vessel. Specifically, the invention provides a method for producing a cell culture vessel suitable for large-capacity culture comprising cutting a long-sized cell support film to obtain a sheet-like cell support film, fixing the film to a first member, which is not closed, and bonding other members thereto. Thus, a cell culture vessel comprising a container section in which a cell (Continued)

support film is fixed to an inner wall surface can be produced.

10 Claims, 21 Drawing Sheets

(51) Int. Cl.
*B32B 37/00* (2006.01)
*C12N 5/071* (2010.01)
*C12M 1/24* (2006.01)
*C12M 1/00* (2006.01)

(58) Field of Classification Search
CPC .. C12M 23/20; B29C 65/00; B29C 66/00145; B29C 66/00; B32B 37/00; B32B 37/10
See application file for complete search history.

(56) References Cited

FOREIGN PATENT DOCUMENTS

| | | |
|---|---|---|
| JP | H0588299 U | 12/1993 |
| JP | 08-116963 | 5/1996 |
| JP | 2001507218 | 6/2001 |
| JP | 2005087005 | 4/2005 |
| JP | 2006517169 | 7/2006 |
| JP | 2008220320 | 9/2008 |
| JP | 201063439 | 3/2010 |
| JP | 201172297 | 4/2011 |
| JP | 2011521642 | 7/2011 |
| WO | 98/24880 | 6/1998 |
| WO | 2004072164 | 8/2004 |
| WO | 2007/097120 | 8/2007 |
| WO | 2009/150931 | 12/2009 |

A

B

A

B

A

B

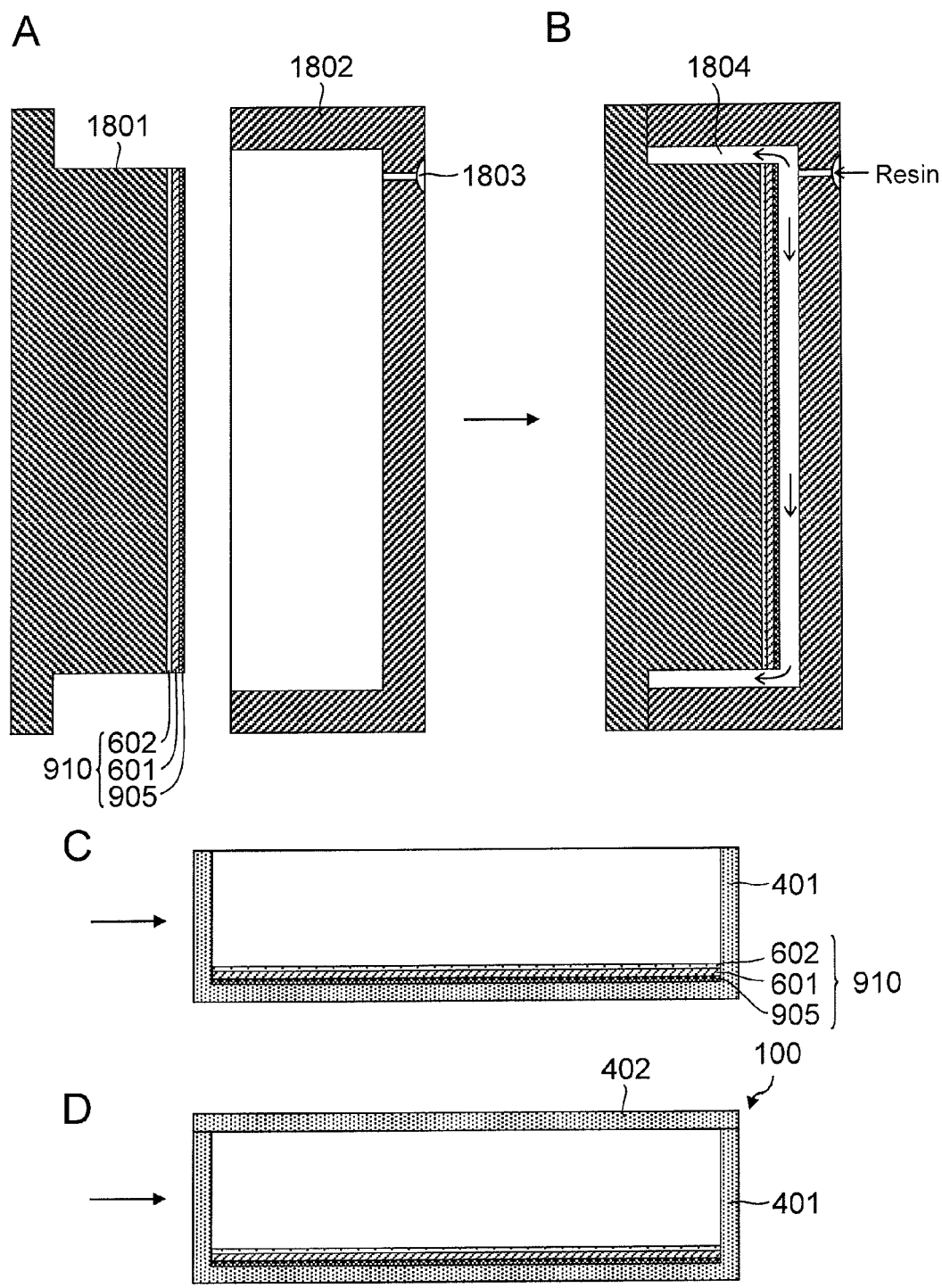

METHOD FOR PRODUCING CELL
CULTURE VESSEL

RELATED APPLICATIONS

This application is a national stage application filed under 35 USC 371 of PCT/JP2012/077843, filed Oct. 29, 2012, which claims the benefit of Japanese Patent Application No. 2011-244719, filed Nov. 8, 2011, all of which are incorporated herein, in entirety, by reference.

TECHNICAL FIELD

The present invention relates to a method for producing a cell culture vessel. More specifically, the present invention relates to a method for producing a flask-type or bottle-type cell culture vessel suitable for mass culture of cells.

BACKGROUND ART

A technique of recovering a cell sheet in a non-invasive manner is reported in, for example, JP Patent Publication H02-211865 A (1990), in which such cell sheet is formed with the use of a temperature-responsive polymer, such as polyisopropylacrylamide. To date, also, dishes and multi-well plates for cell culture using such temperature-responsive polymers have been commercialized and used in the field of regenerative medicine.

SUMMARY OF THE INVENTION

Problem to be Solved by the Invention

In order to realize regenerative medicine, a technique of mass cell culture is necessary. However, areas for cell culture in dishes and multi-well plates are small. In order to perform mass cell culture, accordingly, the use of many culture vessels becomes necessary, which in turn necessitates operations for treating such many culture vessels. Accordingly, development of a cell culture vessel that allows mass cell culture to be performed in a manner that allows cells to be stably detached therefrom and a technique that enables mass-production of such cell culture vessels in a cost-effective manner has been awaited.

As a cell culture vessel suitable for mass culture, for example, a flask-type or bottle-type cell culture vessel equipped with a high-capacity inner chamber that accommodates cells and media is known. The inner wall surface in such a vessel should have a certain degree of detachability, and the inner wall surface should be located in a closed area. Accordingly, establishment of a technique that efficiently provides such area with a certain degree of detachability has been awaited.

Under the above circumstances, it is a primary object of the present invention to provide a cost-effective technique for mass-production of a cell culture vessel that allows mass cell culture to be performed in a manner that allows cells to be stably detached therefrom.

Means for Solving the Problem

The present inventors had completed the present invention described below as a means for solving the above problem.

(1) A method for producing a cell culture vessel comprising a container section in which an inner chamber that accommodates cells and media is provided, the container section comprising a cell support film, which is at least provided with a film substrate layer and, disposed thereon, a stimuli-responsive polymer layer having a cell-adhesive surface capable of changing into a non-cell-adhesive surface upon reception of a particular stimulus, fixed to at least a part of the inner wall surface facing the inner chamber in a manner such that the stimuli-responsive polymer layer is disposed facing the inner chamber, the method comprising:

a step of cutting a long-sized cell support film to prepare a sheet-like cell support film;

a step of cell support film fixation comprising fixing a sheet-like cell support film to a first member of the container section having a region of an opened inner wall surface to which the cell support film is fixed, thereby producing a film-fixed first member; and a step of member bonding for constituting the container section by bonding the film-fixed first member to one or more other members.

(2) The method according to (1), further comprising a step of producing a long-sized cell support film, wherein the step of producing a long-sized cell support film comprises unwinding the rolled long-sized film substrate to feed the unwound film substrate, forming a stimuli-responsive polymer layer on the unwound film substrate, and rewinding the formed film substrate as a roll.

(3) The method according to (1) or (2), wherein the step of cutting comprises cutting the long-sized cell support film to prepare a polygonal sheet-like cell support film.

(4) The method according to any of (1) to (3), wherein the step of cell support film fixation comprises a step of allowing the sheet-like cell support film to adhere to the first member with the aid of an adhesive.

(5) The method according to any of (1) to (3), wherein the step of cell support film fixation comprises a step of fixing the sheet-like cell support film to the first member by heat sealing.

(6) The method according to any of (1) to (3), wherein the step of cell support film fixation comprises a step of fixing the sheet-like cell support film to the first member by ultrasonic welding.

(7) The method according to any of (1) to (3), wherein the step of cell support film fixation comprises a step of fixing the sheet-like cell support film to the first member by laser-beam welding.

(8) The method according to any of (1) to (3), wherein the step of cell support film fixation comprises a step of introducing resin into an injection mold in which the sheet-like cell support film is disposed in advance to prepare the first member and obtaining the film-fixed first member.

(9) The method according to any of (1) to (3), wherein the step of cell support film fixation comprises a step of introducing resin into an injection mold in which the sheet-like cell support film is disposed in advance to prepare the first member and obtaining the film-fixed first member, the cell support film further comprising a heat-sealable resin layer formed on a surface of the film substrate layer opposite from the stimuli-responsive polymer layer.

(10) The method according to any of (1) to (3), wherein the step of cell support film fixation comprises a step of fixing the sheet-like cell support film to the first member with the use of a physical locking means.

(11) The method according to any of (1) to (10), which further comprises a step of sterilization by irradiation of the cell culture vessel with a γ beam under vacuum conditions.

(12) A cell culture vessel comprising a container section in which an inner chamber that accommodates cells and media is provided, the container section comprising a cell support film, which is at least provided with a film substrate layer and, disposed thereon, a stimuli-responsive polymer layer having a cell-adhesive surface capable of changing into a non-cell-adhesive surface upon reception of a particular stimulus, fixed to at least a part of the inner wall surface facing the inner chamber in a manner such that the stimuli-responsive polymer layer is disposed facing the inner chamber.

(13) A cell support film provided with a half-cut long-sized detachable film comprising:

a long-sized cell support film at least comprising a film substrate layer and, disposed thereon, a stimuli-responsive polymer layer, and a long-sized detachable film layer formed on a surface of the film substrate layer of the cell support film opposite from the stimuli-responsive polymer layer, the cell support film comprising a plurality of regions surrounded with cut lines and separable as sheets, and each cut line being a half-cut line reaching to a depth equivalent to the thickness of the cell support film, so that the cell support film is cut in the direction of film thickness, but the detachable film is not completely cut off.

(14) A sheet-like cell support film comprising at least a film substrate layer and, disposed thereon, a stimuli-responsive polymer layer, the sheet-like cell support film being in a shape such that it is able to cover approximately the entire area of the bottom inner surface of the container section of the flask-type cell culture vessel.

Typically, "the sheet-like cell support film being in a shape such that it is able to cover approximately the entire area of the bottom inner surface of the container section of the flask-type cell culture vessel" is a sheet-like cell support film composed of a square region integrated with a trapezoidal region extending from one side of the square region, with such side being designated as a lower base and the upper base being shorter than such lower base, as in the case of the cell support film 610 shown in FIG. 15.

<Other Embodiments of the Present Invention>

The present invention also includes the embodiments described below.

(15) A long-sized cell support film at least comprising a film substrate layer and, disposed thereon, a stimuli-responsive polymer layer, with the stimuli-responsive polymer layer being washed to remove unfixed polymer components and monomer components.

(16) A long-sized cell support film at least comprising a film substrate layer and, disposed thereon, a stimuli-responsive polymer layer, with the stimuli-responsive polymer layer not being washed to remove unfixed polymer components and monomer components.

(17) The long-sized cell support film according to (15) or (16), which further comprises an adhesive layer on a surface of the film substrate layer opposite from the stimuli-responsive polymer layer.

(18) The long-sized cell support film according to (17), which further comprises, on a surface of an adhesive layer, a detachable film layer to protect the adhesive layer and to be detached at the time of use.

(19) The long-sized cell support film according to (15) or (16), which further comprises a heat-sealable resin layer on a surface of the film substrate layer opposite from the stimuli-responsive polymer layer.

(20) A cell support film provided with a half-cut long-sized detachable film comprising the long-sized cell support film according to (15), (16), (17), or (19) and, on a surface thereof (preferably a surface opposite from the stimuli-responsive polymer layer), a detachable film layer detachably adhering thereto, the cell support film comprising a plurality of regions surrounded with cut lines and separable as sheets from outer regions of the cut lines, and each cut line being a half-cut line reaching to a depth equivalent to the thickness of the cell support film, so that the cell support film is cut in the direction of film thickness, but the detachable film is not completely cut off.

According to this embodiment, the plurality of regions surrounded with cut lines of the cell support film are each independently separable as a sheet-like cell support film piece from other regions of the cell support film and the detachable film, and these film pieces can be used in the method for producing a cell culture vessel in the present invention.

(21) A sheet-like cell support film at least comprising a film substrate layer and, disposed thereon, a stimuli-responsive polymer layer, with the stimuli-responsive polymer layer being washed to remove unfixed polymer components and monomer components.

(22) A sheet-like cell support film at least comprising a film substrate layer and, disposed thereon, a stimuli-responsive polymer layer, with the stimuli-responsive polymer layer not being washed to remove unfixed polymer components and monomer components.

(23) The sheet-like cell support film according to (21) or (22), which further comprises an adhesive layer on a surface of the film substrate layer opposite from the stimuli-responsive polymer layer.

(24) The sheet-like cell support film according to (23), which further comprises, on a surface of the adhesive layer, a detachable film layer to protect the adhesive layer and to be detached at the time of use.

(25) The sheet-like cell support film according to (21) or (22), which further comprises a heat-sealable resin layer on a surface of the film substrate layer opposite from the stimuli-responsive polymer layer.

(26) The sheet-like cell support film according to any of (21) to (25), which is in a polygonal shape, such as a triangle, quadrilateral (e.g., a rectangular, quadrate, parallelogram, or rhombic shape), pentagonal, hexagonal, or heptagonal, or octagonal shape, is circular, or is in an ellipsoidal shape.

This description includes part or all of the content as disclosed in the description and/or drawings of Japanese Patent Application No. 2011-244719, which is a priority document of the present application.

Effects of the Invention

The present invention enables efficient production of a flask-type, bottle-type, or other type of cell culture vessel in which an inner chamber for accommodating cells and media is provided, and the inner wall surface of the inner chamber exhibits cell adhesiveness of interest.

BRIEF DESCRIPTION OF THE DRAWINGS

FIG. 12A is a schematic cross-sectional view demonstrating that a laminate is half-cut in the step of cutting, and FIG. 12B schematically demonstrates that a long-sized laminate is half-cut in the step of cutting, so as to prepare a cell support film provided with a long-sized, half-cut, detachable film.

FIG. 21 schematically shows another embodiment of a step of cell support film fixation by in-mold integration and a step of member bonding.

EMBODIMENTS FOR CARRYING OUT THE INVENTION

Hereafter, the features of the present invention are explained with reference to the figures, according to need;

however, it should be noted that the figures are provided for illustrative purposes, and the sizes and the configurations of the components are demonstrated with adequate exaggeration for illustrative purposes.

<Cell Culture Vessel>

The cell culture vessel produced by the present invention is at least provided with a container section in which an inner chamber that accommodates cells and media is provided, and it is further provided with a lid or the like, according to need. Since the capacity of such container section can be easily increased, it is suitable for mass cell culture.

The term "container section in which an inner chamber . . . is provided" refers to the configuration in which such inner chamber is provided within the interior space surrounded by walls that constitute the container section. Specifically, the container section of the present invention is provided with an inner chamber, and the entire periphery is closed by walls constituting the container section; that is, the bottom, the sides, and the upper side of the inner chamber, at the time of cell culture (a through-hole may be provided on part of the wall). Thus, such container is different from a dish- or bowl-type container that is open in an upward direction.

In general, the container section is provided with a through-hole for introducing or discharging cells and media that allows the inner chamber to communicate with the exterior in a part of the container section. It is preferable that a through-hole be closed by a removable lid. It is preferable that the container section provided with a through-hole further comprise a neck extending from the perimeter of a through-hole so as to be directed away from the inner chamber and a detachable lid be mounted on the neck.

Figure 1:
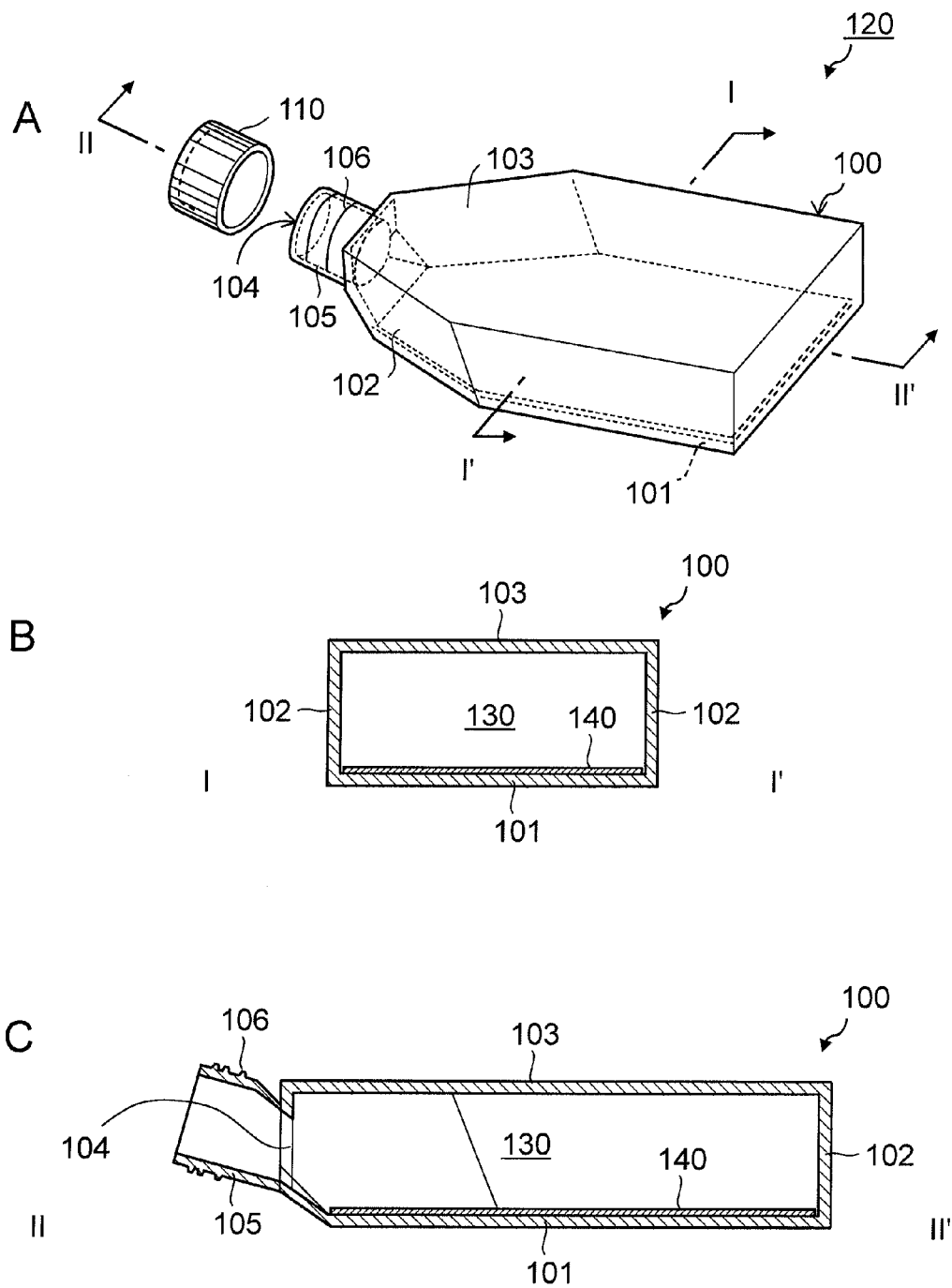
FIG. 1A is a perspective view showing the structure of a flask-type cell culture vessel produced in the present invention.
FIG. 1B is a cross-sectional view of the container section 100 along the line I-I'.
FIG. 1C is a cross-sectional view along the line II-II'.

FIG. 1 shows a container section according to a preferable embodiment. A container section 100 shown in FIG. 1A at least comprises a bottom 101, a side wall 102 vertically arranged along the perimeter of the bottom 101, and a top surface 103 bonded to an upper end of the side wall 102 and opposed to the bottom 101. Such container section is referred to as a "flask-type" container comprising a through-hole 104 that pierces a part of the side wall 102 and a neck 105 extending from the perimeter of the through-hole 104 toward the outside of the container section. A locking member 106 that locks a lid 110 is provided on the neck 105 of the container section 100, and the lid 110 is peelably mounted through the locking member. A flask-type cell culture vessel 120 is formed by joining the container section 100 with the lid 110.

FIG. 1B is a cross-sectional view of the container section 100 along the line and FIG. 1C is a cross-sectional view along the line. An inner chamber 130 that accommodates cells and media is formed in the interior space surrounded by the bottom 101, the side wall 102, and the top surface 103 of the container section 100. A cell support film 140 is fixed to a part of the inner wall surface (the bottom 101 according to the embodiment shown in FIG. 1) facing the inner chamber 130.

Figure 2:
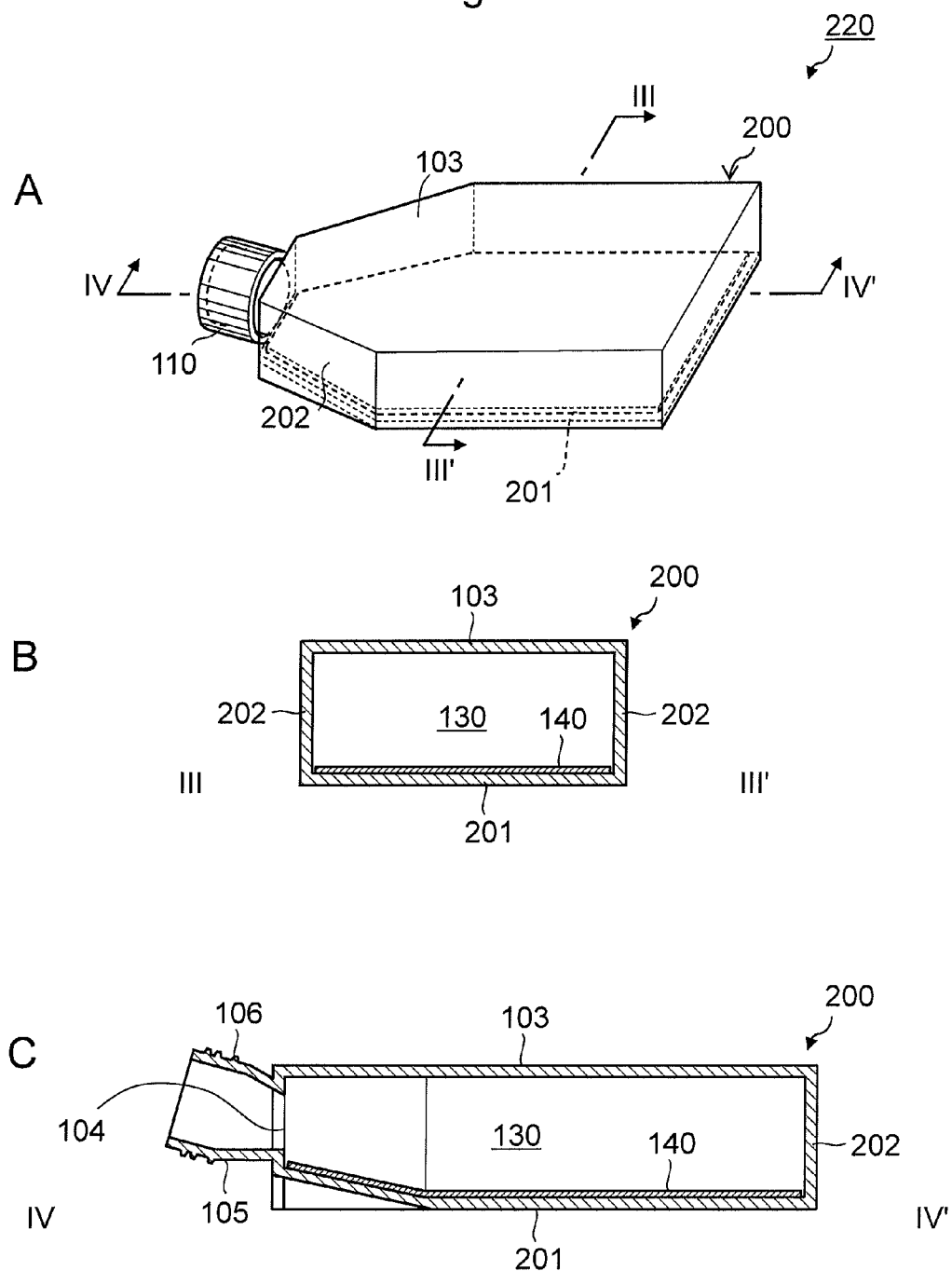
FIG. 2A is a perspective view showing the structure of a flask-type cell culture vessel produced in the present invention.
FIG. 2B is a cross-sectional view of the container section 200 along the line III-III'.
FIG. 2C is a cross-sectional view along the line Iv-IV'.

FIG. 2 shows a flask-type container section according to another preferable embodiment. In the container section 200 shown in FIG. 2A, a part of the bottom 201 is bent toward a top surface 103. The side walls 202 are provided standing on the peripheral edges of the bottom 201, and these walls connect the bottom 201 to the top surface 103 disposed opposite thereto. A container section 200 having such configuration is also classified as being of the "flask-type."

Figure 3:
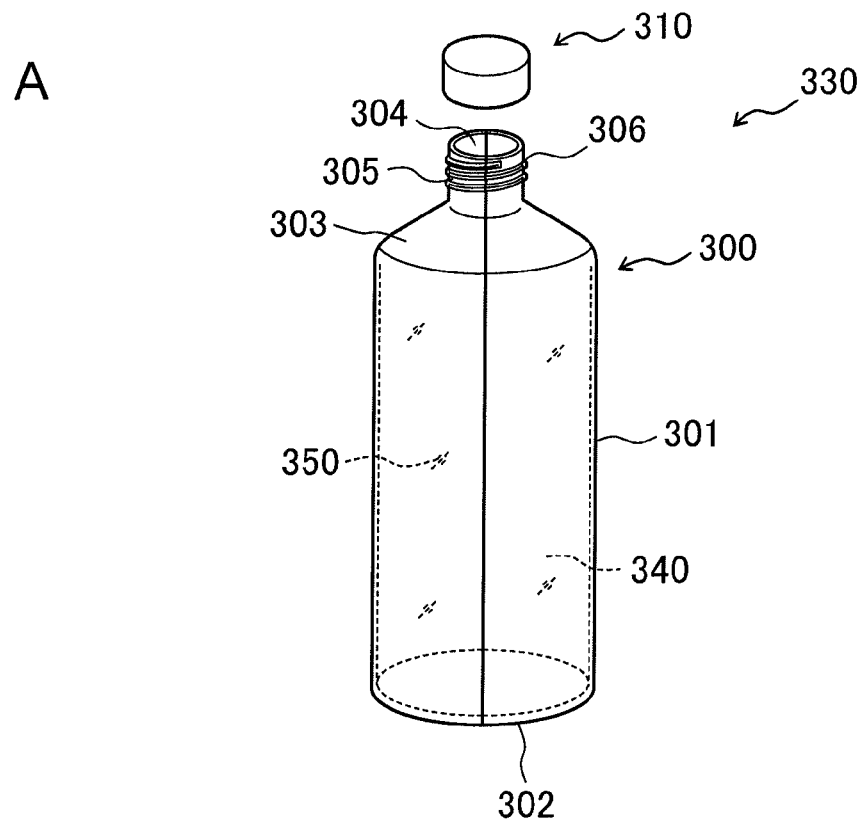
FIG. 3A is a perspective view showing a structure of a bottle-type cell culture vessel produced in the present invention.
FIG. 3B shows the structure of members used for producing the container section of the bottle-type cell culture vessel produced in the present invention.
Figure 3:
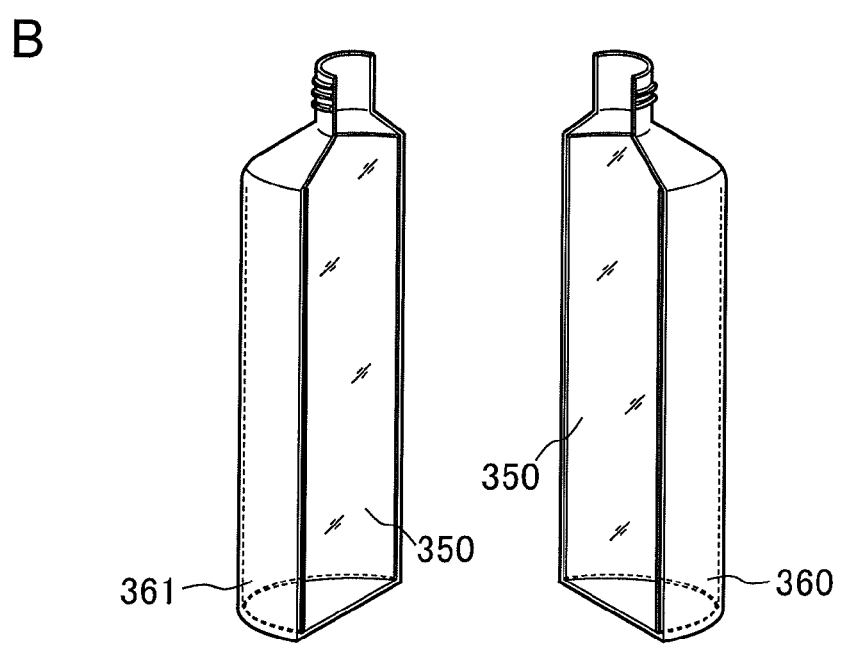

As shown in FIG. 3A, a container section according to another embodiment is a bottle-type container section comprising a tubular body 301, a bottom 302 bonded to close an end of the body 301, and an apex 303 bonded to close the other end of the body 301. In such container section, a through-hole 304 is provided in a part of the apex 303, and a neck 305 extends from the periphery of the through-hole 304 to the outside of the container section. The neck 305 is provided with a locking member 306 to lock a lid 310, and the lid 310 is peelably mounted thereon through the locking member 306. Such container section 300 is referred to as a "bottle-type" container. An inner chamber 340 that accommodates cells and media is provided in the interior space of the container section 300. A cell support film 350 described below is fixed to an inner wall surface facing the inner chamber 340 of the body 301. FIG. 3A shows an example in which the body 301 is in a tubular form with a circular cross section, although the shape of the body 301 is not limited thereto. If the body is in a tubular form, a cross section thereof may be in any form. For example, the body may be a polygon, such as a triangle, quadrilateral, pentagon, or hexagon.

Materials that constitute other members of a cell culture vessel, such as a container section and a lid, are not particularly limited, and common materials for cell culture can be used. Examples include: resin materials, such as polystyrene resin, polyester resin, polyethylene resin, polyethylene terephthalate resin, polypropylene resin, ABS resin, nylon, acrylic resin, fluorocarbon resin, polycarbonate resin, polyurethane resin, methylpentene resin, phenolic resin, melamine resin, epoxy resin, and vinyl chloride resin; resin materials containing at least one of the aforementioned resin materials having hydrophilized surfaces; and inorganic materials, such as glass and quartz, with resin materials being preferable. It is preferable that a resin material be polystyrene or polyethylene terephthalate.

In the container section of the present invention, the inner wall surface to which the cell support film is to be fixed is not exposed to the outside, and another region of the inner wall surface of the container section (e.g., a top surface 103 disposed opposed the bottom 101 to which the cell support film 140 is to be fixed in the case of the embodiment shown in FIG. 1) is disposed thereto. Thus, it is not easy to introduce or to fix the cell support film to the inner wall surface of the inner chamber after the production of the container section is completed. In order to facilitate the fixation of the cell support film, in the present invention, a first member comprising an inner wall surface, which is not closed, to which a cell support film is to be fixed and one or more other members are prepared, the cell support film is fixed to the first member, and the first member to which the film has been fixed is then bonded to one or more other members. Thus, the container section is produced.

Figure 4:
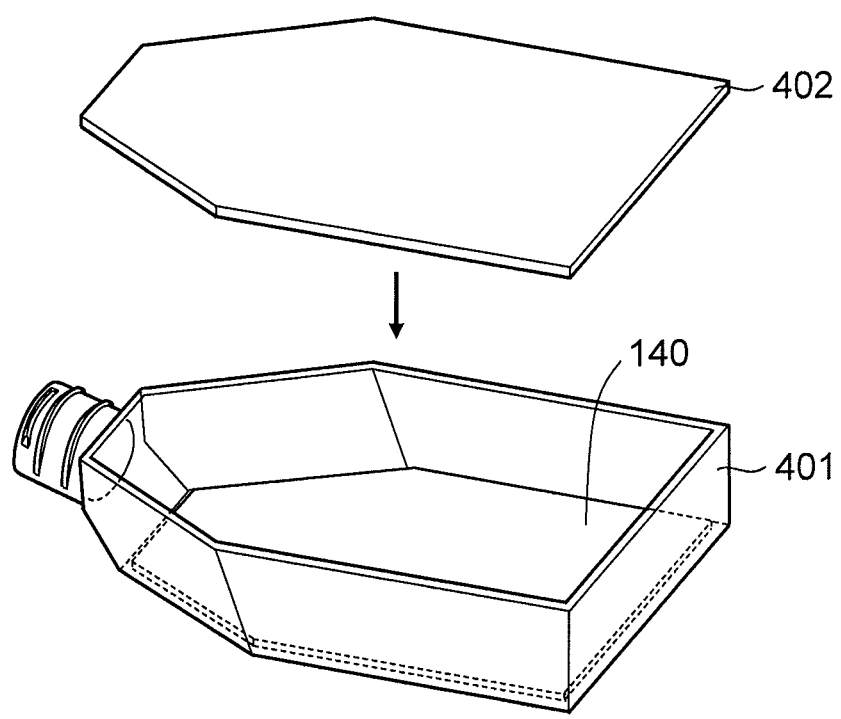
FIG. 4 is an explanatory view demonstrating a process of producing a flask-type cell culture vessel by bonding a first member to another member.

Production of a container section with the combined use of a plurality of members is described in greater detail with reference to FIG. 4 and FIG. 5. According to an embodiment of the production of the container section 100, as shown in FIG. 4, a first member 401 comprising a bottom 101 having an opened side to which the cell support film 140 is to be fixed and a side wall 102 is bonded to a second member 402, which is a top surface 103. Thus, the container section 100 is formed. Before the first member 401 is bonded to the second member 402, the cell support film 140 is fixed to the inner wall surface of the bottom 101 of the first member 401. In the present invention, a first member to which a cell support film is fixed, in particular, is referred to as a "film-fixed first member." The first member 401 to which the cell support film 140 is fixed (shown in FIG. 4) can also be referred to as a "film-fixed first member." The first member 401 is bonded to the second member 402 in accordance with the purpose of cell culture. If necessary, these members are bonded to each other in a fluid-tight manner, so as to prevent a culture solution from leaking.

Figure 5:
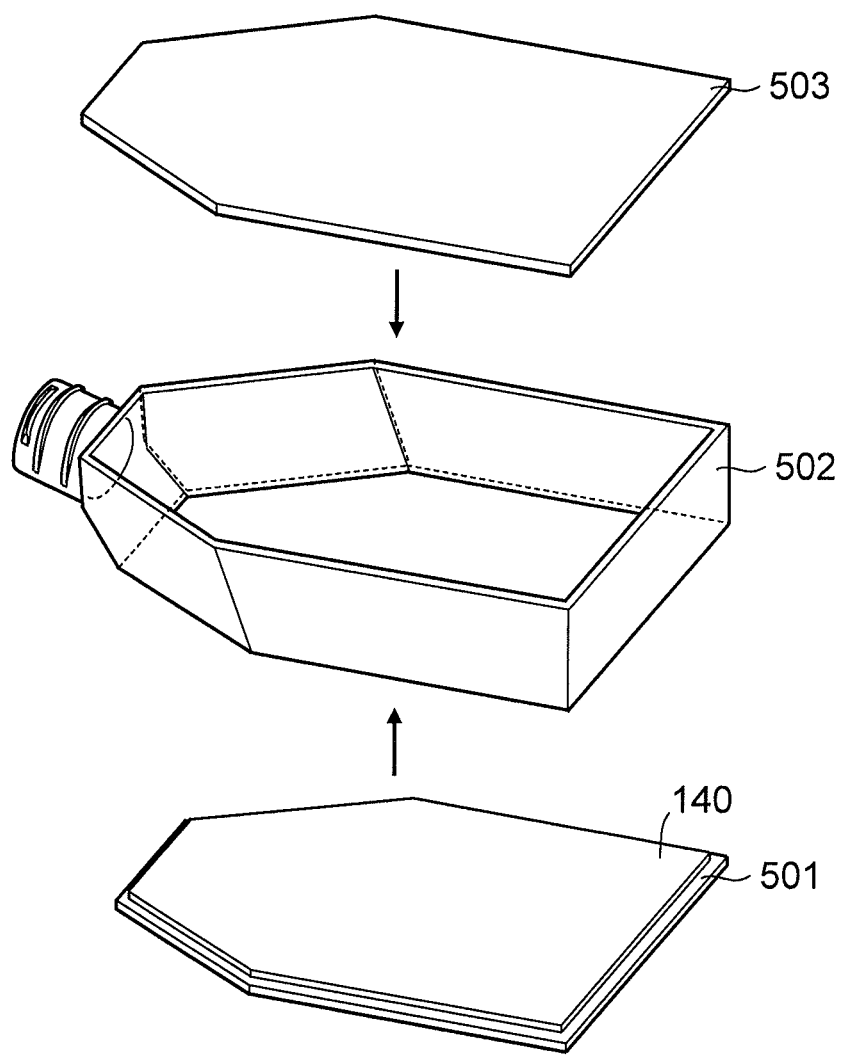
FIG. 5 is an explanatory view demonstrating a process of producing a flask-type cell culture vessel by bonding a first member to two other members.

According to an embodiment shown in FIG. 5, the container section 100 is formed by bonding the first member 501 (i.e., the bottom 101), the second member 502 (i.e., the side wall 102 provided with the neck 105), and the third member 503 (i.e., the top surface 103). The cell support film 140 is fixed to a region of the first member 501 (i.e., the inner wall surface of the bottom 101).

Combinations of a plurality of members are not limited to those shown in FIGS. 4 and 5.

In order to produce a container section, one or more first members may be used. When cell support films are to be fixed to a plurality of inner wall surfaces of an inner chamber of the container section disposed opposed to each other, for example, a plurality of inner wall surfaces are prepared as first members, and the cell support films are fixed to such plurality of first members by the method of the present invention. Thus, pluralities of film-fixed first members are formed. In the step of member bonding, a plurality of film-fixed first members are further bonded to other members, according to need, and the production of the container section is thus completed. A plurality (n number) of film-fixed first members may be bonded to each other to complete the production of the container section. In such a case, the remaining n−1 number of film-fixed first members bonded to a film-fixed first member are regarded as "one or more other members" in the step of member bonding. In the case of a bottle-type container section 300 comprising a cell support film 350 fixed to an inner surface of a body 301 as shown in FIG. 3A, for example, two first members having approximately the same configuration are prepared by dividing the container section 300 along the shaft center of the body 301, a cell support film is fixed to each thereof to prepare film-fixed first members, and these two film-fixed first members (360 and 361 in FIG. 3B) are bonded to produce a container section 300. In such a case, either the member 360 or 361 can serve as "one or more other members" in the step of member bonding.

In the present invention, commercialized products may be purchased and used as members constituting the cell culture vessel, as well as first member(s) and one or more other members for producing the container part. Also, a person who employs the method of the present invention may produce such members. The first member(s) and one or more other members used for producing a container section made of resin materials can be produced by, for example, injection molding of resin, and providing the surface of such member(s) with a scale used for measurement of the volume of the content by printing or other means, according to need. Alternatively, resin may be introduced into an injection mold in which the sheet-like cell support film has been disposed in advance, so as to simultaneously perform the formation of the first member and the formation of the film-fixed first member.

<Structure of Cell Support Film>

The structure of the cell support film according to the present invention is described with reference to FIG. 6 to FIG. 9.

A cell support film 610 at least comprises a film substrate layer 601 and, disposed thereon, a stimuli-responsive polymer layer 602 having a cell-adhesive surface capable of changing into a non-cell-adhesive surface upon reception of a particular stimulus.

It is preferable that the cell support film 610 be flexible in an unwound state, so that it can be rewound as a roll.

The cell support film 610 can further comprise a necessary layer in accordance with the method of bonding thereof to a member constituting the cell culture vessel.

Figure 7:
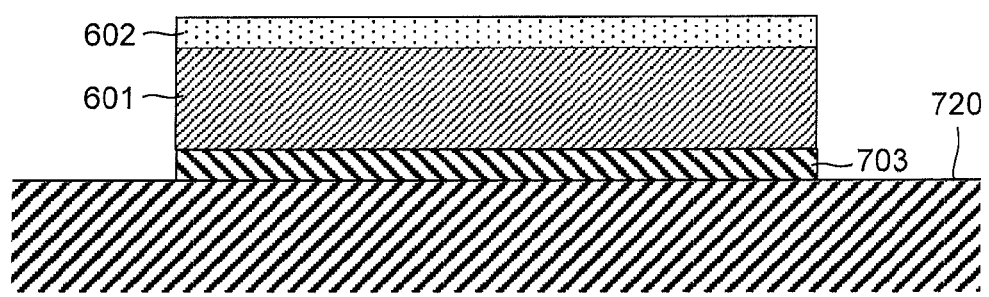
FIG. 7 schematically shows a condition in which a cell support film is bonded to a surface of the first member with the aid of an adhesive.
Figure 8:
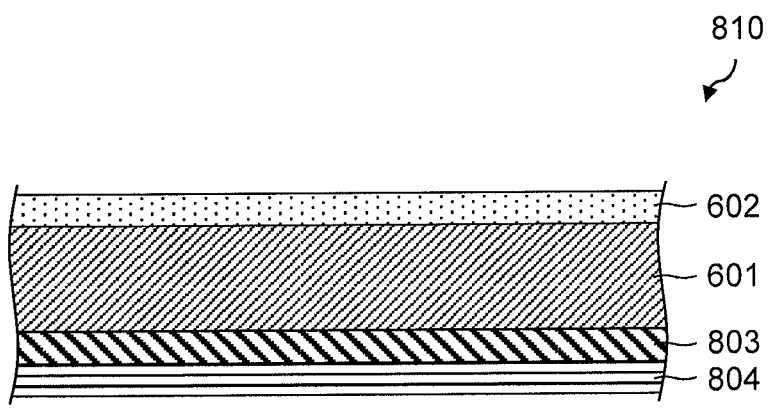
FIG. 8 schematically shows an embodiment of a cross section of a cell support film.

For example, the cell support film 610 can be adhered to the first member 720 with the aid of an adhesive 703 on the surface of the film substrate layer 601 opposite from the stimuli-responsive polymer layer 602, as shown in FIG. 7. In such a case, a cell support film 810 further provided with an adhesive layer 803 can be used, as shown in FIG. 8. Before the film is adhered, the surface of the adhesive layer 803 of the cell support film 810 can be further protected with a detachable film 804, according to need.

Figure 9:
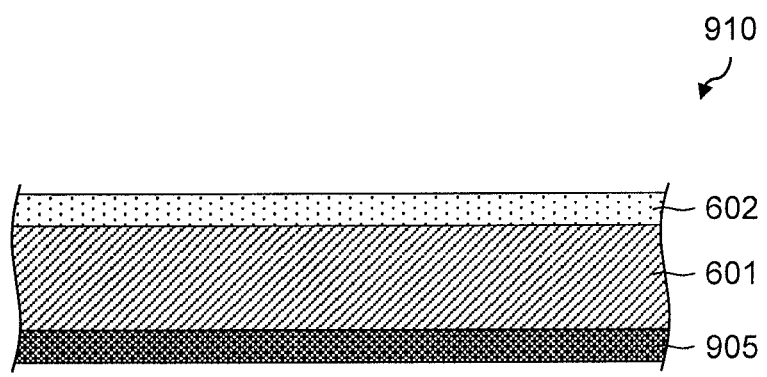
FIG. 9 schematically shows an embodiment of a cross section of a cell support film.

Also, the surface of the film substrate layer 601 of the cell support film 610 on which the stimuli-responsive polymer layer 602 is provided can be fixed to the first member by heat sealing, according to need. In such a case, a cell support film 910 further provided with a heat-sealable resin layer 905 can be used, as shown in FIG. 9.

A stimuli-responsive polymer layer comprises a polymer, cell-adhesiveness of the surface of which changes by the particular stimulus. Examples of stimuli-responsive polymers include a temperature-responsive polymer, a pH-responsive polymer, an ion-responsive polymer, and a light-responsive polymer, and the temperature-responsive polymer is particularly preferable because a stimulus can be easily applied thereto.

For example, use of a temperature-responsive polymer exhibiting cell adhesiveness at a temperature at which cells are cultured and exhibiting non-cell-adhesiveness at a temperature at which the prepared cell sheet is detached is preferable. For example, a preferable temperature-responsive polymer exhibits enhanced affinity for water in the vicinity thereof at a temperature below the critical solution temperature, and such polymer swells upon water uptake, which makes it difficult for the cells to adhere to the surface (i.e., non-cell-adhesiveness). In contrast, such polymer is dehydrated and contracts at a temperature equivalent to the critical solution temperature or higher, which allows cells to easily adhere to the surface (i.e., cell adhesiveness). Such critical solution temperature is referred to as the lower critical solution temperature. The lower critical solution temperature (T) of a temperature-responsive polymer is preferably 0° C. to 80° C., and more preferably 0° C. to 50° C.

Specific examples of temperature-responsive polymers that can be suitably used in the present invention include acrylic polymers and methacrylic polymers. More specific examples include poly-N-isopropylacrylamide (T=32° C.), poly-N-n-propylacrylamide (T=21° C.), poly-N-n-propylmethacrylamide (T=32° C.), poly-N-ethoxyethyl acrylamide (T=about 35%), poly-N-tetrahydrofurfurylacrylamide (T=about 28° C.), poly-N-tetrahydrofurfurylmethacrylamide (T=about 35° C.), and poly-N,N-diethylacrylamide (T=32° C.). Alternatively, a copolymer of two or more types of monomers constituting such polymers may be used.

As monomers constituting such polymers, monomers that can be polymerized through exposure to radiation can be used. Examples of such monomers include a (meth)acrylamide compound, an N-(or N,N-di)alkyl-substituted (meth)acrylamide derivative, a (meth)acrylamide derivative having a cyclic group, and a vinyl ether derivative. One or more such monomers can be used. When monomers of the same type are used, a polymer formed on a substrate is a homopolymer. When plural types of monomers are used in combination, a polymer formed on a substrate is a heteropolymer. Both types of polymers are within the scope of the present invention.

When it is necessary to adjust "T" because of the type of grown cells, when it is necessary to enhance the interaction between the coating material and a cell culture support, or when it is necessary to adjust the hydrophilic/hydrophobic balance of the cell support, for example, monomers other than those described above may further be added to prepare copolymers. Further, graft or block copolymers of the aforementioned polymers used in the present invention and other polymers or mixtures of the polymers of the present invention and other polymers may be used. As long as the properties inherent to polymers are maintained, polymers may be subjected to crosslinking.

pH-responsive polymers and ion-responsive polymers that are suitable for cell sheets to be prepared can be adequately selected.

A stimuli-responsive polymer is fixed on the surface of a film substrate layer to a given thickness to prepare a stimuli-responsive polymer layer. The film thickness is, for example, preferably between 0.5 nm and 300 nm, and more preferably between 1 nm and 100 nm. By adjusting the film thickness between 0.5 nm and 300 nm, adhesion and detachment of cells can be easily carried out. A stimuli-responsive polymer layer may contain a surfactant or other components, provided that functions thereof are not affected.

Cell adhesiveness and non-cell-adhesiveness represent the relative correlations between a region and another region in terms of the degrees of cell adhesion.

The term "cell adhesiveness" refers to the property whereby cells easily adhere. Cell adhesiveness is determined based on whether or not cells are likely to adhere or extend due to chemical, physical, or other surface properties.

As an indicator for evaluating cell adhesiveness, the degree of cell adhesion/extending observed at the time of actual cell culture can be used. It is preferable that a cell-adhesive surface exhibit a 60% or higher degree of cell adhesion/extending, with the surface exhibiting a degree of cell adhesion/extending of 80% or higher being more preferable. With a high degree of cell adhesion/extending, cell culture can be efficiently carried out. In the present invention, the degree of cell adhesion/extending is defined as follows. Cells to be cultured at a seeding density from 4,000 cells/cm$^2$ to less than 30,000 cells/cm$^2$ are seeded on the surface of the target analyte, the resultant is stored in an incubator at 37° C. in the presence of 5% $CO_2$, and the percentage of cells that have adhered or extend after culture has been conducted for 14.5 hours is determined (i.e., {(the number of adhered cells)/(the number of seeded cells)}×100 (%)).

Cells are seeded by preparing a suspension of cells in a DMEM medium containing 10% FBS, seeding the resulting cell suspension onto the target analyte, and then slowly shaking the target analyte onto which cells have been seeded, so as to extend the cells as uniformly as possible. Further, the degree of cell adhesion/extending is determined by exchanging media immediately before measurement so as to remove the cells that have not adhered. The degree of cell adhesion/extending is measured at sites other than sites that are likely to exhibit specific cell density (e.g., the center of a given region in which cell density is likely to increase or the periphery of a given region in which cell density is likely to decrease).

The term "non-cell-adhesiveness" refers to the property whereby cells adhere with difficulty. Non-cell-adhesiveness is determined based on whether or not cells are likely to adhere or extend due to chemical, physical, or other surface properties.

The degree of cell adhesion/extending of a non-cell-adhesive surface is preferably less than 60%, more preferably less than 40%, further preferably 5% or less, and the most preferably 2% or less.

<Film Substrate Layer>

A surface of the film substrate layer may be composed of a material capable of forming the stimuli-responsive polymer layer described above, and the type of material is not particularly limited. Typical examples of materials for the film substrate layer include polyethylene terephthalate (PET), polystyrene (PS), polycarbonate (PC), triacetyl cellulose (TAC), polyimide (PI), nylon (Ny), low-density polyethylene (LDPE), medium-density polyethylene (MDPE), vinyl chloride, vinylidene chloride, polyphenylene sulfide, polyethersulfone, polyethylene naphthalate, polypropylene, and acrylic polymers. Biodegradable polymers, such as polylactic acid, polyglycolic acid, polycaprolactam, or a copolymer thereof, may also be used. Preferable examples include polyethylene terephthalate, polystyrene, and polycarbonate.

A surface of a film substrate layer onto which a stimuli-responsive polymer layer is provided can be subjected to adhesion-increasing treatment. The term "adhesion-increasing treatment" refers to treatment with, for example, an adhesion-increasing agent, such as polyester, acrylic ester, polyurethane, polyethyleneimine, a silane coupling agent, or perfluorooctane sulfonic acid (PFOS). Specifically, the film substrate layer comprising an easy-adhesion surface onto which a stimuli-responsive polymer layer is to be provided is composed of a layer comprising the material described above and an easy-adhesion layer comprising the adhesion-increasing agent provided on at least one surface of the aforementioned layer.

A commercially available film substrate layer with an easy-adhesion surface may be used, according to need.

Film substrate layer thickness (i.e., the entire thickness of a film substrate layer, including an easy-adhesion layer, when the film substrate layer comprises an easy-adhesion layer in addition to the substrate layer) is not particularly limited. A film with a preferable thickness is sufficiently flexible to allow it to be rewound as a roll. For example, such preferable thickness is 5 μm to 500 μm, preferably 20 μm to 400 μm, and more preferably 50 μm to 250 μm.

<Formation of Stimuli-Responsive Polymer Layer>

In the present invention, a stimuli-responsive polymer layer can be formed on a film substrate layer in the manner described below. Specifically, a coating composition comprising monomers to be polymerized and an organic solvent capable of dissolving such monomers is prepared, and a film substrate surface is coated with the resulting composition in accordance with a conventional technique. Subsequently, the resulting coating is subjected to adequate processing, such as exposure to radiation, to allow polymerization of monomers in the coating, and graft polymerization reactions are allowed to proceed between a film substrate surface and a polymer. Thus, a stimuli-responsive polymer layer can be formed on a film substrate layer.

An organic solvent capable of dissolving monomers is not particularly limited, provided that it is capable of dissolving monomers. An organic solvent having a boiling point of 120° C. or lower, and particularly 60° C. to 110° C., at normal pressures is preferable. Specific examples of preferable solvents include methanol, ethanol, n-propanol, 2-propanol, n-butanol, 2-butanol, and water, and such solvents may be used in combination. Other solvents, such as 1-pentanol, 2-ethyl-1-butanol, 2-butoxyethanol, or ethylene (or diethylene)glycol or its monoethyl ether, may also be used. Other additives may be added to the solution, according to need.

According to a preferable embodiment of the present invention, 2-propanol (isopropyl alcohol) is used as an organic solvent capable of dissolving monomers. It is preferable that monomer content in the coating composition be 5% to 70% by weight. In addition to monomers, the coating composition may contain an oligomer or prepolymer resulting from polymerization of a plurality of monomers. According to this embodiment, the oligomer or prepolymer size is not particularly limited, provided that the oligomer or prepolymer is at least a dimer. An oligomer or prepolymer with a molecular weight of approximately 3,300 (typically a 28-molecule polymer) is preferable, and an oligomer or prepolymer with a molecular weight of 5,700 or higher is more preferable.

Examples of radiation sources to be used for polymerization and grafting include α rays, β rays, γ rays, electron beams, and ultraviolet rays. In order to manufacture the desired graft polymer, γ rays and electron beams are preferable because of their high energy efficiency, with electron beams being particularly preferable from the viewpoint of productivity. Ultraviolet rays can be used in combination with a suitable polymerization initiator or an agent anchored to the film substrate surface.

The radiation dosage of electron beams is preferably in the range of 5 Mrad to 50 Mrad, and that of γ rays is preferably in the range of 0.5 Mrad to 5 Mrad.

After the step of irradiation, the coating is dried so as to remove the organic solvent, according to need.

The thus-formed stimuli-responsive polymer layer may further be subjected to washing, according to need. It is considered that, on the surface of the stimuli-responsive polymer layer after graft-polymerization, unfixed free polymer molecules and unreacted monomers are present, in addition to polymer molecules immobilized by covalent binding. Washing is preferable since such free polymer or unreacted molecules can be removed thereby. The method of washing is not particularly limited, and typical examples include immersion washing, swing washing, shower washing, spray washing, and ultrasonic washing. In addition, typical examples of a washing solution include various water-based washing solutions, alcohol-based washing solutions, hydrocarbon-based washing solutions, chlorine-based washing solutions, and acid/alkali washing solutions.

<Adhesive Layer>

Examples of adhesive agents constituting an adhesive layer include polyester resin, acrylic ester resin, polyurethane resin, polyethyleneimine resin, a silane coupling agent, and perfluorooctane sulfonic acid (PFOS), with acrylic ester resin, polyurethane resin, or the like being particularly preferable.

The thickness of an adhesive layer is not particularly limited. It is preferably between 10 μm and 300 μm, and more preferably between 20 μm and 200 μm.

Before the adhesive layer 803 is allowed to adhere to the first member, it is preferable that a detachable film layer 804 that protects the adhesive layer 803 be applied to the outer surface of the adhesive layer 803 of the cell support film 810, as shown in FIG. 8. The detachable film layer 804 is composed of a detachable member, and it is removed from the adhesive layer 803 at the time of adhesion. A detachable member is not particularly limited, provided that it has sufficient strength and flexibility. Examples include resin films made of polyethylene terephthalate, polypropylene, and polyethylene and foam films thereof that have been made detachable with the use of a silicone-based, fluorine-based, long-sized-chain alkyl-group-containing carbamate, or other peeling agent. The thickness of the detachable film 804 is not particularly limited, and it is preferably between 10 μm and 100 μm.

The adhesive layer 803 can be formed by applying a coating solution for forming an adhesive layer that contains an adhesive and, according to need, a solvent to a surface of a film substrate or detachable film, and drying the coating, according to need. Examples of coating methods include comma coating, blade coating, gravure coating, rod coating, knife coating, reverse roll coating, and offset gravure coating.

<Heat-Sealable Resin Layer>

A heat-sealable resin layer is a heat-sensitive adhesive (i.e., an adhesive that becomes molten upon heating and adheres to a target object). A heat-seal layer is applied in advance, and it allows a film to adhere to a target with the application of heat or pressure at the time of use.

A heat-sealable resin layer can be formed by a printing method, such as gravure coating, dye coating, roll coating, or spray coating.

<Method for Producing Cell Culture Vessel>

Figure 20:
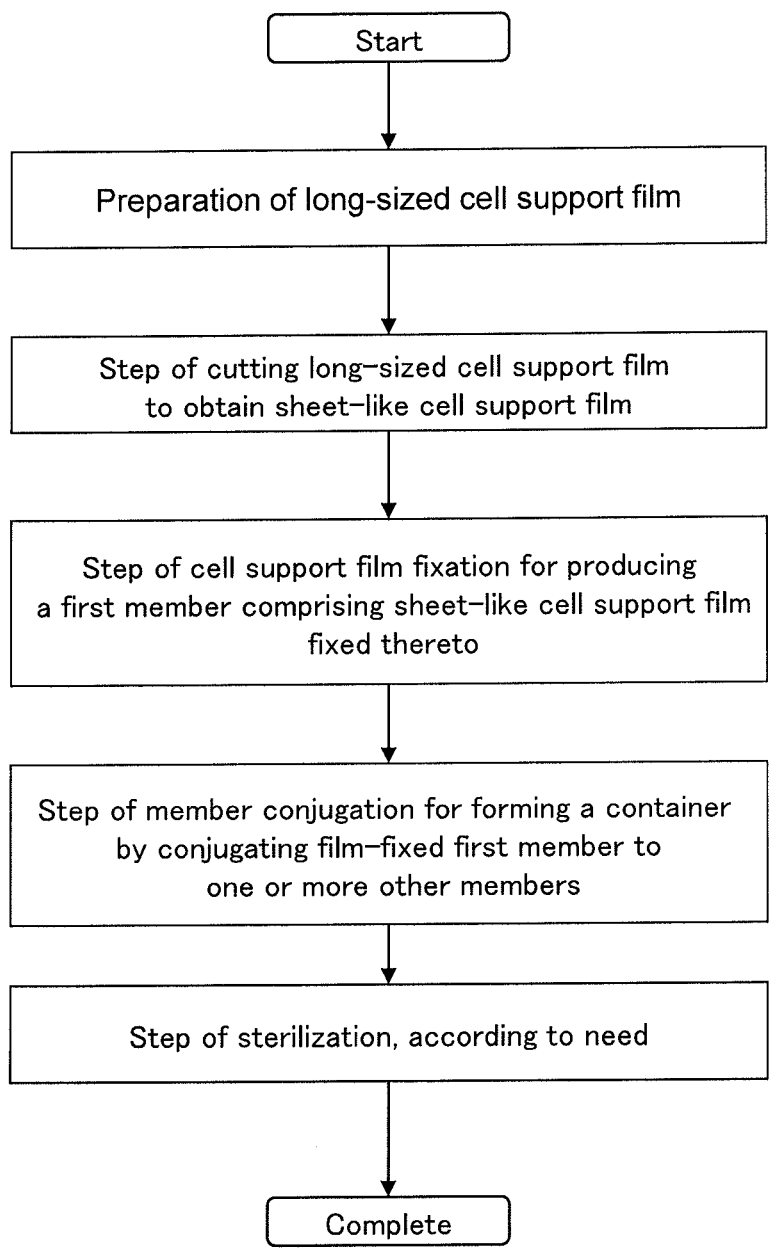
FIG. 20 is a flow diagram schematically showing the method for producing the cell culture vessel of the present invention.

As schematically shown in FIG. 20, the method for producing the cell culture vessel of the present invention comprises preparing a long-sized cell support film and successively performing a step of cutting, a step of cell support film fixation, and a step of member bonding. In addition to the above steps, a step of sterilization is occasionally performed, according to need. Hereafter, these steps are described in detail, although the present invention is not limited to the embodiments described below.

<Preparation of Cell Support Film>

In the present invention, a step of preparing a long-sized cell support film is occasionally referred to as a "step of cell support film preparation."

A step of cell support film preparation is a step of preparing a long-sized cell support film. The term "preparing a long-sized cell support film" preferably refers to the production of a long-sized cell support film. Alternatively, a long-sized cell support film that has been produced in advance may be prepared in this step. Hereafter, the former step of producing a long-sized cell support film is referred to as a "step of cell support film production."

In the step of cell support film production, it is preferable that the long-sized cell support film be produced by a roll-to-roll method. According to the roll-to-roll method, a flexible long-sized substrate wound as a roll is unwound, the substrate is subjected to a given treatment with intermittent or continuous feeding, and the substrate is rewound as a roll. In comparison with the batch system whereby cell support films are produced sheet-by-sheet, cell support films with higher uniformity can be efficiently produced by the roll-to-roll method.

According to an embodiment of the step of cell support film production, a long-sized film substrate wound as a roll is unwound and fed, a stimuli-responsive polymer layer is formed on the unwound film substrate, and the formed film substrate is rewound as a roll.

Figure 10:
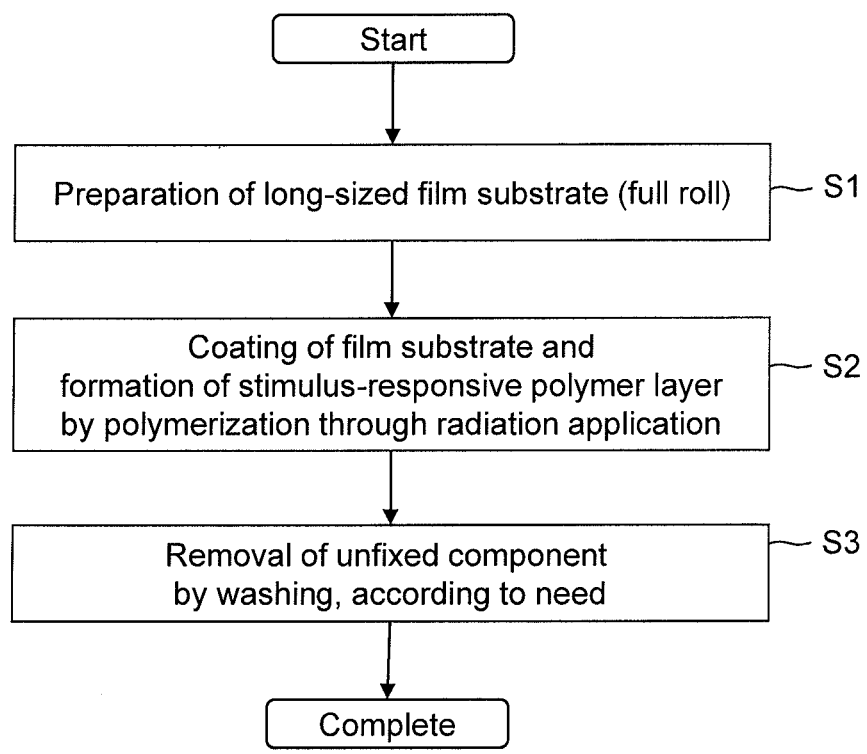
FIG. 10 schematically shows a method for producing a cell support film.

A method for producing a cell support film 610 comprising a film substrate layer 601 and a stimuli-responsive polymer layer 602 by the roll-to-roll method is described with reference to FIG. 10. At the outset, a long-sized film substrate wound as a roll (a full roll) is prepared (S1). A film substrate with a surface that was subjected to adhesion-increasing treatment in advance may be used. A film substrate may be subjected to adhesion-increasing treatment by the roll-to-roll method, according to need. A film substrate wound as a roll is unwound and fed, the surface of the unwound film substrate is coated with a coating composition at least comprising monomers for forming a stimuli-responsive polymer and a solvent, the coating is irradiated with radiation, such as via an electron beam, and graft polymerization reactions are allowed to proceed between the surface and a stimuli-responsive polymer (S2). Subsequently, monomers remaining unreacted or polymers remaining ungrafted as a result of the roll-to-roll method are removed by washing in accordance with the means described above, according to need (S3). Thus, a long-sized cell support film can be obtained (the completion of production).

Examples of methods for producing the cell support film 810 comprising the adhesive layer 803 superposed thereon and the protective detachable film layer 804 adhering thereto (shown in FIG. 8) include the methods (1) to (3) described below:

(1) a method comprising: a step of preparing an intermediate product 1 of the long-sized cell support film comprising a film substrate layer 601 and a stimuli-responsive polymer layer 602 superposed thereon by the method described above; a step of unwinding to feed the intermediate product 1 of the long-sized cell support film wound as a roll and forming an adhesive layer 803 on the film substrate layer 601 of the intermediate product 1 of the cell support film by the method described above with regard to the adhesive layer; and a step of causing the long-sized detachable film 804 to adhere to the adhesive layer 803 and rewinding the resulting cell support film 810 as a roll;

(2) a method comprising: a step of preparing an intermediate product 1 of the long-sized cell support film comprising a film substrate layer 601 and a stimuli-responsive polymer layer 602 superposed thereon by the method described above; a step of producing an intermediate product 2 of the long-sized cell support film comprising a long-sized detachable film 804 and an adhesive layer 803 superposed thereon by the roll-to-roll method or providing the intermediate product 2 of the long-sized cell support film that was produced in advance; and a step of adhering the intermediate product 1 of the long-sized cell support film to the intermediate product 2 of the cell support film in a manner such that the film substrate layer 601 of the intermediate product 1 of the cell support film is brought into contact with the adhesive layer 803 of the intermediate product 2 of the cell support film to produce the long-sized cell support film 810 provided with the detachable film layer 804, and rewinding the resulting long-sized cell support film 810 as a roll; and (3) a method comprising: a step of producing an intermediate product 3 of the long-sized cell support film comprising a film substrate 601, an adhesive layer 803, and a detachable film layer 804 superposed thereon by the roll-to-roll method or providing the intermediate product 3 of the long-sized cell support film that was produced in advance; and a step of forming a stimuli-responsive polymer layer 602 on the film substrate layer 601 of the intermediate product 3 of the long-sized cell support film by the method described above and rewinding the resulting long-sized cell support film 810 provided with the detachable film layer 804 as a roll.

As shown in FIG. 9, the long-sized cell support film 910 further comprising the heat-sealable resin layer 905 superposed thereon can also be produced by forming the film substrate layer 601, the heat-sealable resin layer 905, and the stimuli-responsive polymer layer 602 by the roll-to-roll method in an arbitrary order. An intermediate product 4 of the cell support film comprising the long-sized film substrate layer 601 and the heat-sealable resin layer 905 superposed thereon that was produced in advance may be prepared and the stimuli-responsive polymer layer 602 may be formed thereon.

<Step of Cutting>

A step of cutting comprises cutting a long-sized cell support film to obtain a sheet-like cell support film.

Figure 11:
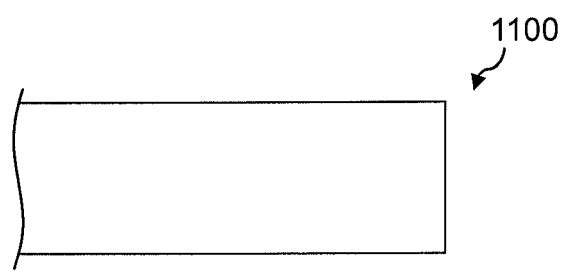
FIG. 11 schematically shows an embodiment of a step of cutting.
Figure 11:
Figure 11:
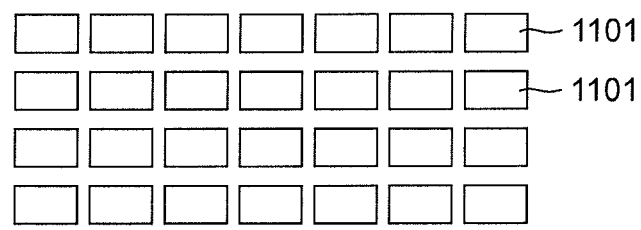
Figure 12:
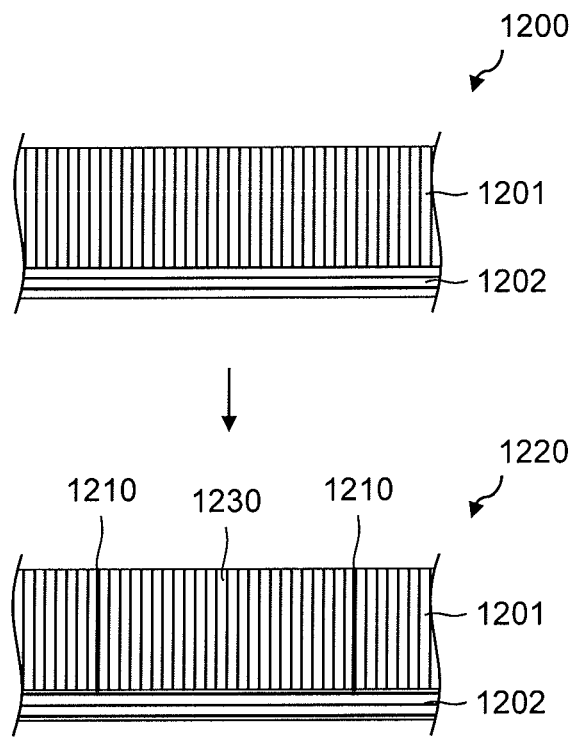
FIG. 12 schematically shows an embodiment of a step of cutting.
Figure 12:
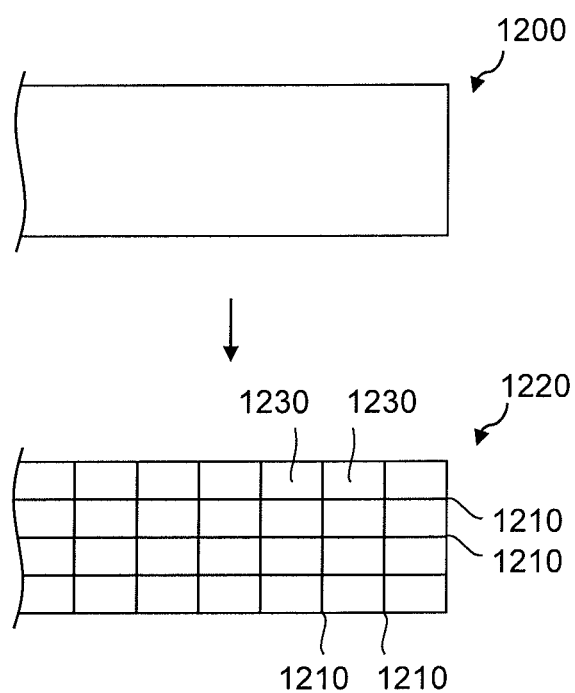

In the step of cutting, typically, a long-sized cell support film 1100 is cut so as to obtain a plurality of separate sheet-like cell support film pieces 1101, as shown in FIG. 11. However, the step of cutting is not limited thereto, and a cell support film may be cut into a sheet form by a so-called "half-cut" technique in this step. Specifically, the detachable film layer 1202 is allowed to adhere to a surface of the long-sized cell support film 1201 opposite from the stimuli-responsive polymer layer in such a manner that it can be detached from the support film, so as to prepare a long-sized, half-cut laminate 1200, as shown in FIG. 12. In the step of cutting, a cut line (i.e., a half-cut line) 1210 is provided from the surface of the cell support film 1201 to reach a depth equivalent to the thickness thereof, so that the cell support film is cut in the direction of film thickness, but the detachable film 1201 is not completely cut off. Thus, a plurality of regions 1230 surrounded with the cut lines 1210 and separable as sheets are provided on the cell support film 1201, and the cell support film 1220 provided with a long-sized, half-cut detachable film are obtained. According to this embodiment, a plurality of regions 1230 of the cell support film 1201 surrounded with the cut lines 1210 can be independently separated from other regions of the cell support film and the detachable film as sheet-like cell support film pieces, and such separate film pieces can be used for the method for producing the cell culture vessel of the present invention. Typically, a half-cut laminate 1200 is the cell support film 810 laminated with the detachable film 804, as shown in FIG. 8. The laminate is not limited thereto, and a cell support film with another structure to which a film layer is detachably adhered may also be used.

A sheet-like cell support film obtained in the step of cutting may be in any form in accordance with a configuration of the region of the first member to which the cell support film is to be fixed. For example, it can be in a polygonal shape, such as a triangle, quadrilateral (e.g., a rectangular, quadrate, parallelogram, or rhombic shape), pentagonal, hexagonal, heptagonal, or octagonal shape, it can be circular, or it can be in an ellipsoidal shape. It is particularly preferable that the sheet-like cell support film be in a polygonal shape, so that sheet-like pieces can be efficiently obtained from the long-sized cell support film. Among various polygonal shapes, a rectangular or quadrate shape is particularly preferable.

<Step of Cell Support Film Fixation>

In the step of cell support film fixation, a film-fixed first member composed of a first member that is a region of an opened inner wall surface to which the cell support film is fixed, and a sheet-like cell support film fixed thereto is produced.

A first member is not particularly limited, provided that it is a region of a container section having an opened inner wall surface on which a cell support film is to be fixed, as the first members 401 and 501 as shown in FIG. 4 and FIG. 5, respectively. Since the inner wall surface on which the first member of the cell support film is to be fixed is not closed, the cell support film can be easily fixed thereto.

A cell support film can be fixed to a first member by any of a variety of techniques. Representative examples are described below.

Figure 13:
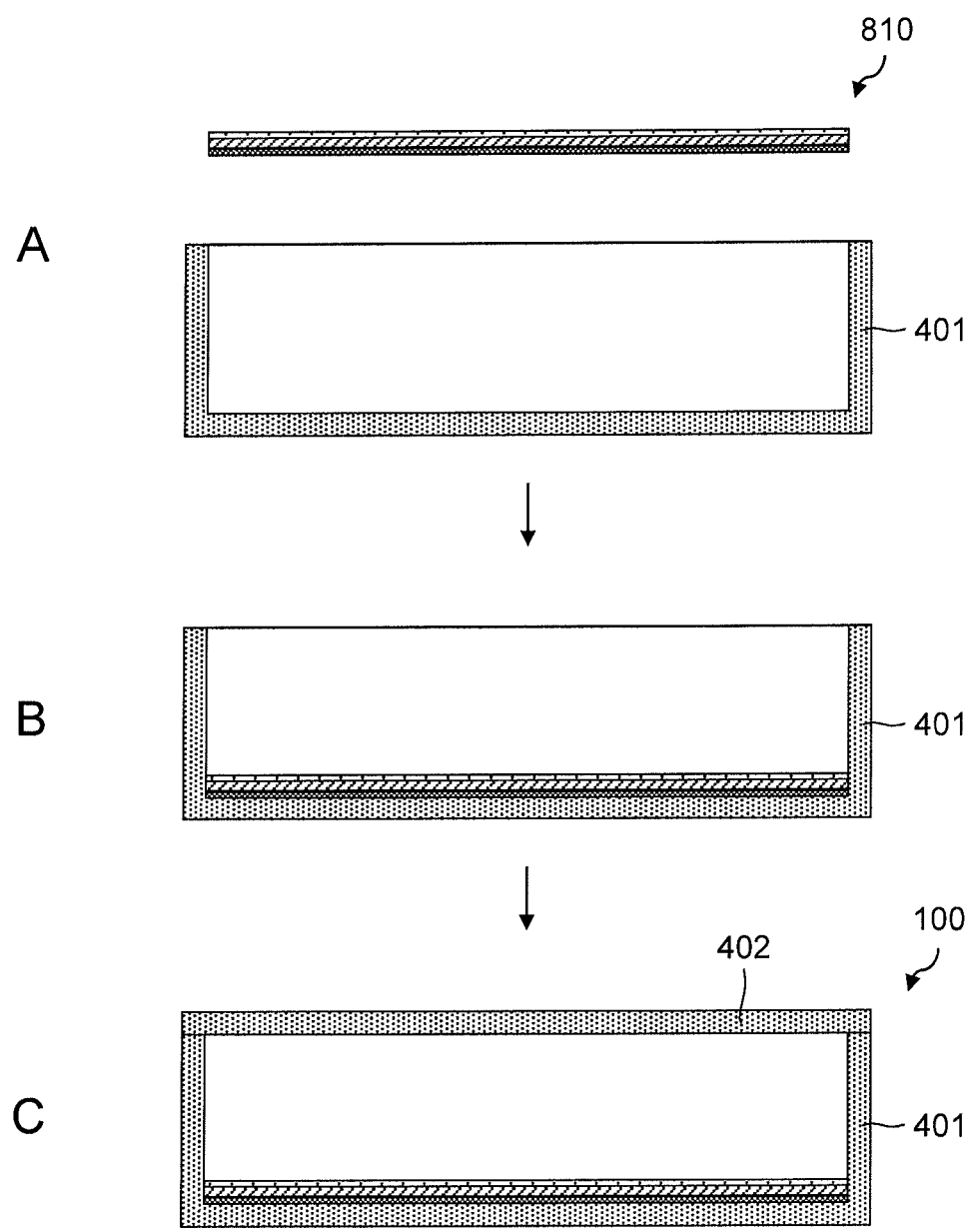
FIG. 13 schematically shows an embodiment of a step of cell support film fixation with the aid of an adhesive and a step of member bonding.

According to the step of cell support film fixation of another embodiment, a sheet-like cell support film is allowed to adhere to a first member with the use of an adhesive layer. According to this embodiment, the cell support film 610 is fixed to the first member 720 with the use of the adhesive 703, as shown in FIG. 7. The cell support film 610 may be adhered to the first member 720 by applying an adhesive to either or both the cell support film 610 and the first member 720. Preferably, the cell support film 810 comprising the detachable film layer 804 adhering thereto as shown in FIG. 8 is prepared, the detachable film layer 804 is removed, and the cell support film 810 is fixed to the first member with the aid of the adhesive layer 803. In FIG. 13, A to C show the step of adhering the cell support film 810 to the first member 401 with the aid of the adhesive layer 803 shown in FIG. 4 (i.e., the I-I' cross section as shown in FIG. 1). The cell support film 810 can be adhered to the first member using a labeler for labeling applications.

After the cell support film is adhered to the first member, the resultant can be subjected to autoclave treatment, according to need, to remove foam on the surface to which the cell support film has adhered.

Figure 14:
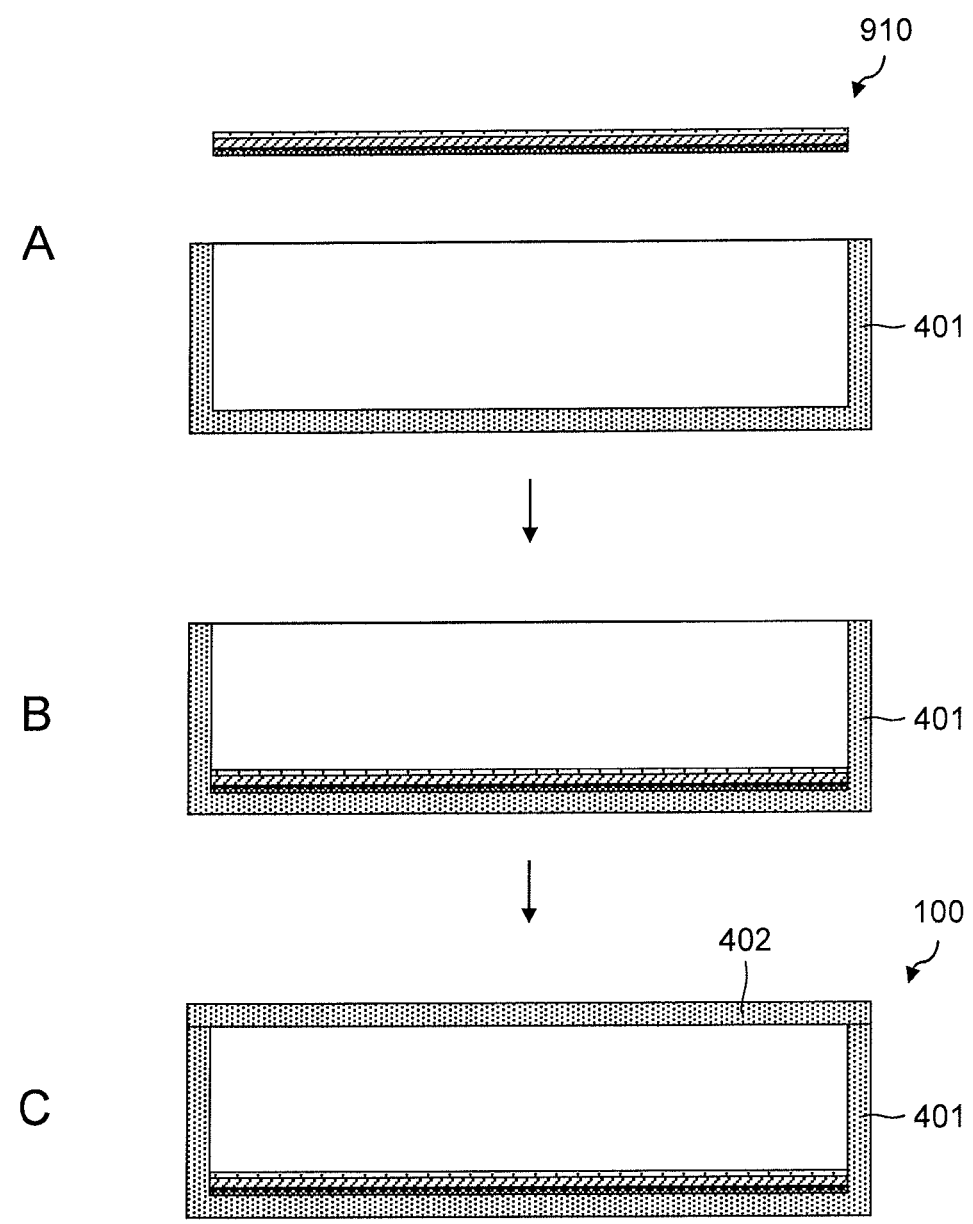
FIG. 14 schematically shows an embodiment of a step of cell support film fixation by heat sealing and a step of member bonding.

According to the step of cell support film fixation of another embodiment, for example, a sheet-like cell support film is fixed to a first member by heat sealing. According to this embodiment, the cell support film 910 comprising the heat-sealable resin layer 905 thereon is disposed on the surface of the first member in such a manner that the heat-sealable resin layer 905 is brought into contact with the first member, as shown in FIG. 9, and they are fixed to each other by heating. In FIG. 14, A to C show the step of adhering the cell support film 910 to the first member 401 with the aid of the heat-sealable resin layer 905 shown in FIG. 4 (i.e., the I-I' cross section as shown in FIG. 1).

Figure 6:
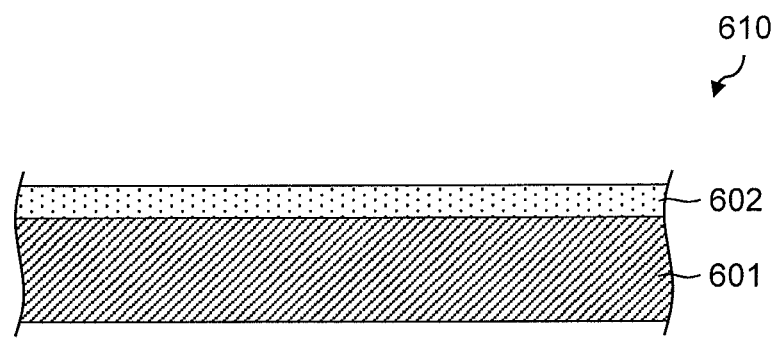
FIG. 6 schematically shows an embodiment of a cross section of a cell support film.

The heat-sealable resin layer 905 is not always necessary for fixation by heat sealing. When the film substrate layer 601 of the cell support film 610 as shown in FIG. 6 is a thermoplastic resin film and the first member is also composed of a thermoplastic resin member, for example, they may be superposed on each other, following which the resultant becomes molten as a result of heating at adequate temperature, and the resultant is then cooled. Thus, heat sealing can be completed.

Figure 15:
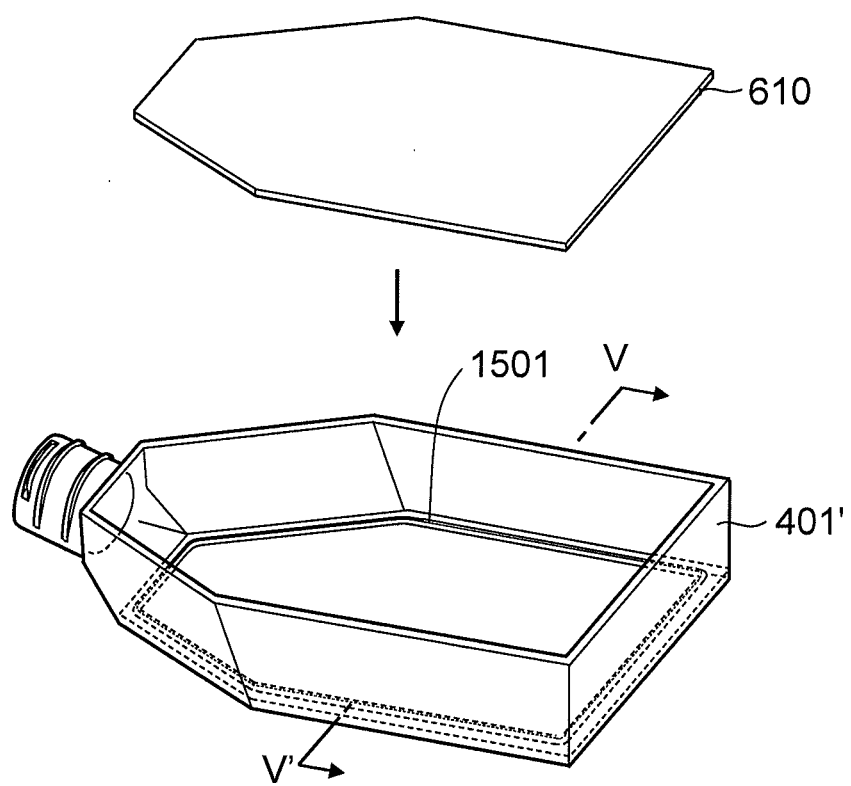
FIG. 15 schematically shows an outline of an embodiment of a step of fixing a cell support film to a first member by ultrasonic welding.
Figure 16:
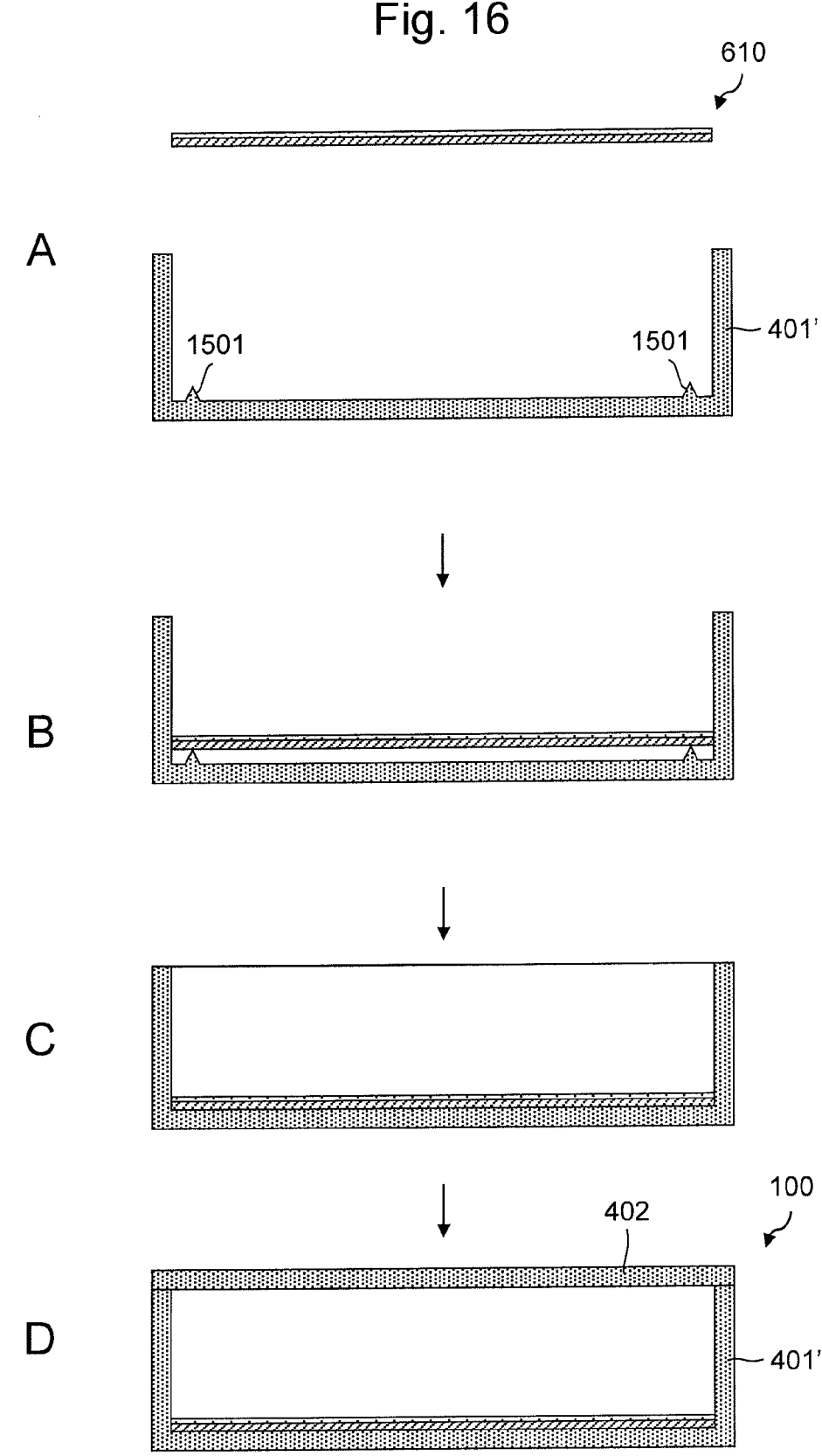
FIG. 16 schematically shows an embodiment of a step of cell support film fixation by ultrasonic welding and a step of member bonding.

According to the step of cell support film fixation of another embodiment, the first member is welded to the sheet-like cell support film by ultrasonic welding. Ultrasonic welding is generally employed for bonding of resin members. Typically, a first member 401' comprising an energy director 1501 necessary for ultrasonic welding (i.e., a thin resin protrusion with a width of about 100 to 1,000 μm and a height of 50 to 1000 μm) integrated with other components is prepared in the periphery of a region of the first member 401 to which the cell support film 601 is to be fixed, as shown in FIG. 15. Subsequently, the cell support film 610 comprising the film substrate layer 601 and the stimuli-responsive polymer layer 602 is brought into contact with an inner bottom region of the first member 401'. With reference to FIG. 16 (i.e., the view along the V-V' cross section shown in FIG. 15), more specifically, the cell support film 610 is mounted on the first member 401', ultrasonic oscillations are applied to a region in which the energy director 1501 is present by pushing a ultrasonic horn against the cell support film 610, and the cell support film 610 is thus fixed to the bottom surface of the first member 401' (FIG. 16C).

Figure 17:
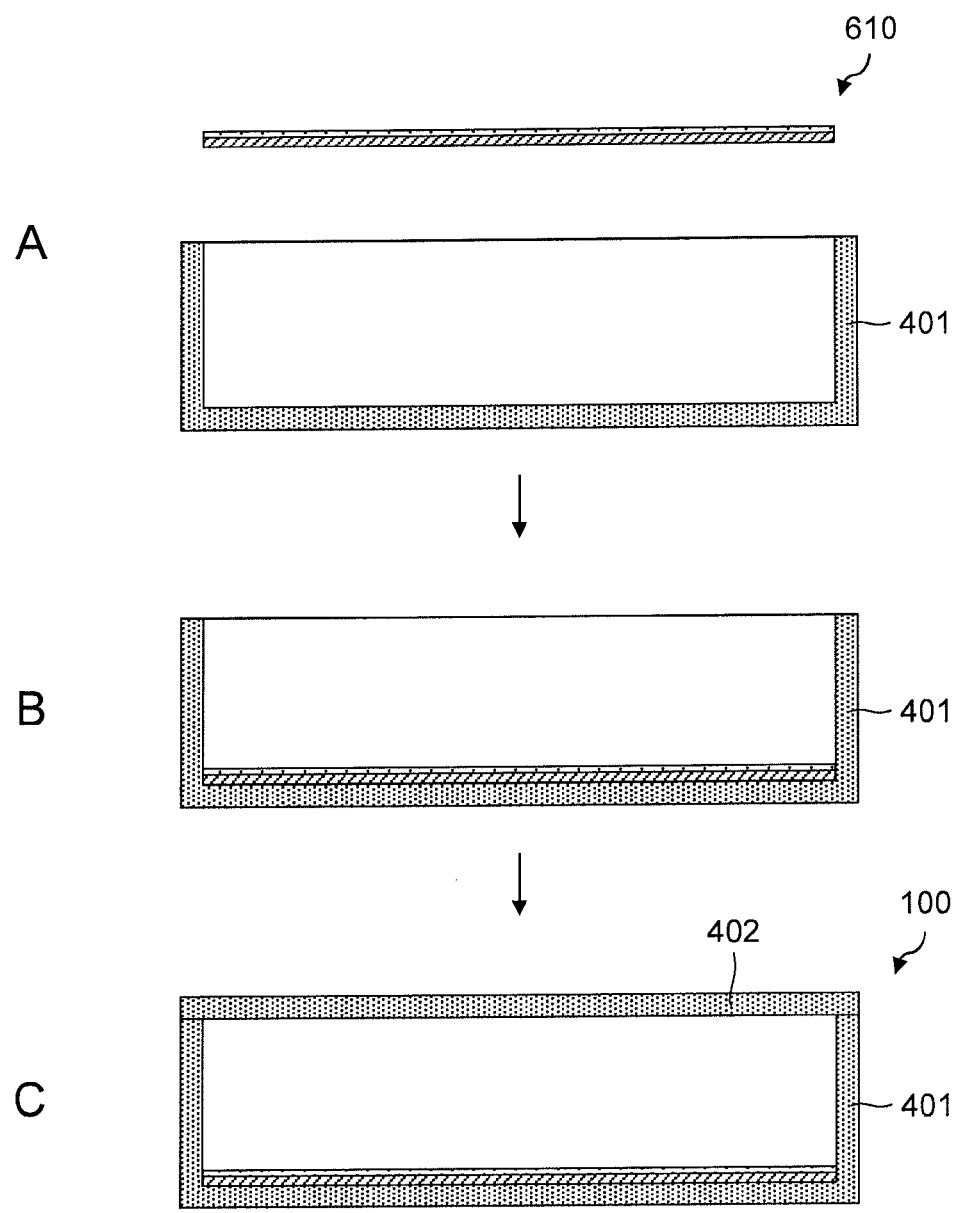
FIG. 17 schematically shows an embodiment of a step of cell support film fixation by laser-beam welding and a step of member bonding.

According to the step of cell support film fixation of another embodiment, the first member is welded to the sheet-like cell support film by laser-beam welding. Laser-beam welding is carried out by superposing a light-transmitting resin member and a light-absorbing resin member and applying laser beams to these members while pushing them against each other to thermally melt the interface between the members. When the cell support film 610 provided with the film substrate layer 601 and the stimuli-responsive polymer layer 602 is bonded to the first member 401, as shown in FIG. 17, one of the surface of the film substrate layer 601 to be fixed to the surface of the first member 401 may be made of a light-transmitting resin member, and the other may be made of a light-absorbing resin member. Thus, laser-beam welding can be carried out.

Figure 18:
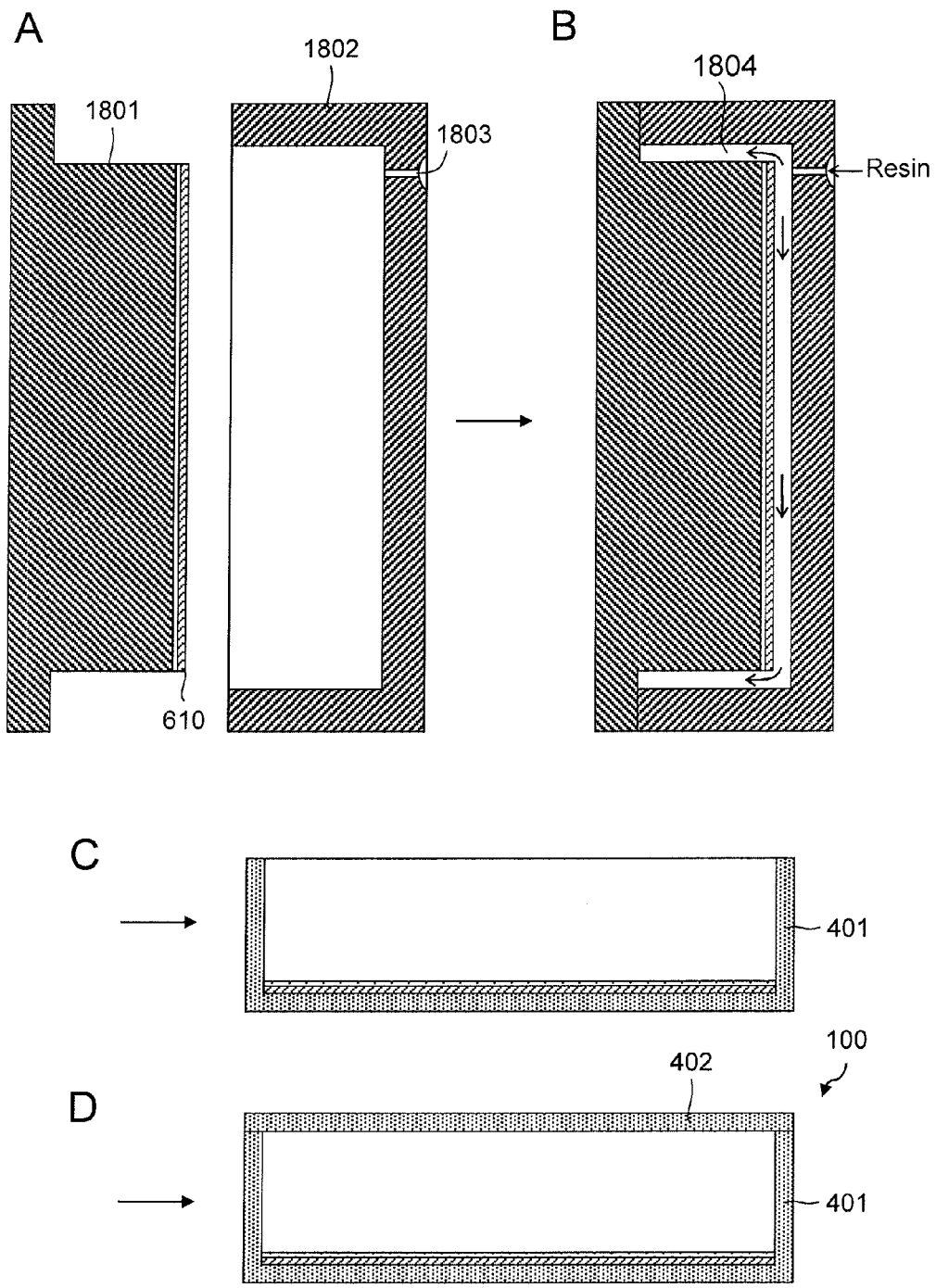
FIG. 18 schematically shows an embodiment of a step of cell support film fixation by in-mold integration and a step of member bonding.

According to the step of cell support film fixation of another embodiment, resin is introduced into an injection mold in which a sheet-like cell support film is disposed in advance to produce a first member, and the film-fixed first member is produced. This method is a type of in-mold forming. The first member 401 comprising the film substrate layer 601 fixed to the bottom thereof produced by this method is described with reference to FIG. 18. In an injection mold involving the use of a convex mold (core) 1801 forming a mold space 1804, which is the first member 401, in combination with a concave mold (cavity) 1802 at the time of mold clamping of the first member 401, a sheet-like cell support film 610 provided with the film substrate layer 601 and the stimuli-responsive polymer layer 602 is disposed in a position of the first member 401 to which the cell support film 610 is to be fixed after the resin has been introduced and has solidified, and the mold is then clamped. Subsequently, molten resin is introduced into the mold through a gate 1803 with the application of injection pressure (FIG. 18B). Thereafter, the mold is opened after the resin has solidified, and a first member 401 comprising the cell support film 610 fixed thereto is then obtained (FIG. 18C).

According to another embodiment, a cell support film 910 further provided with a heat-sealable resin layer 905 instead of the cell support film 610 on the surface of the film substrate layer 601 opposite from the stimuli-responsive polymer layer 602 is used. In an injection mold involving the use of the convex mold 1801 in combination with the concave mold 1802, as shown in FIG. 21, the cell support film 910 is disposed in the mold in such a manner that at least a part of the surface of the heat-sealable resin layer 905 (the entire surface in FIG. 21) is exposed to a mold space and the surface of the stimuli-responsive polymer layer 602 is brought into contact with the inner wall surface of the mold. Thereafter, the mold is clamped. Subsequently, molten resin is introduced into the mold through the gate 1803 with the application of injection pressure, the mold is opened after the resin has solidified, and a first member 401 comprising the cell support film 910 fixed thereto is obtained (FIG. 21C). According to this embodiment, the heat-sealable resin layer 905 becomes molten upon contact with high-temperature molten resin, and it is solidified as the resin is solidified. Thus, the film substrate layer 601 is strongly bonded to the first member 401.

According to the step of cell support film fixation of another embodiment, a sheet-like cell support film is locked with the first member with the aid of a physical locking means. The physical locking means is not particularly limited, provided that it is capable of fixing the cell support film to a given position of the first member. For example, a hook provided on the first member may be used in combination with a through-hole provided on the sheet-like cell support film and serving as a hook acceptor to be locked with the hook. Alternatively, a concave portion provided on the first member may be used in combination with a convex portion provided on the sheet-like cell support film and serving as a concave portion acceptor to be locked with the concave portion.

<Step of Member Bonding>

A step of member bonding comprises bonding a film-fixed first member comprising a cell support film fixed to a given position of the first member to one or more other members, so as to form a container section.

In the film-fixed first member, a cell support film is fixed to an opened inner wall surface, as shown in FIGS. 4 and 5. When other members of the container section are joined with the first member, a container section comprising an inner chamber in which the cell support film of the first member is disposed on the inner wall surface is constituted. In the resulting container section, a region facing the cell support film is closed, namely such region is closed by the inner wall surface (which may have a through-hole). One or more other members can be used in combination. The number of other members is preferably 3 or less, and more preferably 2 or 1.

The first member and one or more other members constituting the container section are composed of various materials, such as resin materials described in connection with the container section. The first member and one or more other members can be bonded in accordance with the purpose of cell culture. These members are bonded to each other in a liquid-tight manner so as to prevent the culture solution from being leaked, if necessary. Members comprising resin materials can be bonded to each other by ultrasonic welding, laser-beam welding, heat sealing, or other means, and members comprising different materials can be bonded to each other by any means, such as adhesion with the use of an adhesive.

In the examples shown in FIGS. 13, 14, 16, 17, and 18, a cell support film is fixed, the second member 402 is bonded to the first member 401 or 401', and production of the container section 100 is then completed.

The container section produced through bonding may be joined with other member, such as a lid, according to need. Thus, the cell culture vessel of the present invention can be obtained.

<Step of Sterilization>

It is preferable that the method of the present invention further comprise a step of sterilizing the cell culture vessel of the present invention.

Examples of sterilization techniques that can be employed include γ ray sterilization, ethylene oxide gas sterilization, electron beam sterilization, ultraviolet ray sterilization, hydrogen peroxide sterilization, and ethanol sterilization. γ ray sterilization is particularly preferable since all species of organisms can be destroyed thereby.

In the present invention, γ ray sterilization is preferable, and γ ray sterilization in vacuo is particularly preferable. In general, commercialized cell culture vessels, such as petri dishes, are often subjected to post-production γ ray sterilization in the air. The present inventors discovered that functions of the stimuli-responsive polymer layer often deteriorated when the cell culture vessel of the present invention was subjected to γ ray sterilization in the air, as described in the examples. This is considered to result from the reaction occurring between oxygen in the air activated by γ ray sterilization and the stimuli-responsive polymer layer. When γ ray sterilization is carried out in vacuo, however, deterioration in functions of the stimuli-responsive polymer layer can be insignificant. Thus, γ ray sterilization is preferably carried out in vacuo.

As a method of γ ray sterilization in vacuo, a method comprising vacuum-packaging a cell culture vessel and irradiating the packaged culture vessel with γ rays from the outside of the package is preferable in terms of convenience. The sterilized and vacuum-packaged cell culture vessel obtained by this method can be shipped as a product in such state.

The γ ray energy to be applied for the purpose of sterilization is preferably between 5 kGy and 30 kGy.

EXAMPLES

Example 1

Adhesion with the Use of Adhesive

A. Production of Temperature-Responsive Cell Support Film

N-Isopropylacrylamide was dissolved in isopropyl alcohol to result in a final concentration of 40% by weight in order to prepare a coating solution. A full roll of an easy-adhesion polyethylene terephthalate film (a 17-cm-wide band) coated with an adhesive and protected with a detachable film (Transparent 50-F Sepa 1090, available from SANKO SANGYO CO., LTD.) was prepared. The film was fed out of the full roll, the coating solution was applied to the film surface by gravure coating, and the coated film was dried by being passed through a hot-air drier at 40° C. for 10 seconds. The coated film was irradiated with electron beams to graft-polymerize N-isopropylacrylamide, poly-N-isopropylacrylamide was fixed to the film surface, and the film was washed to remove unfixed components. Thus, a long-sized cell support film comprising a polyethylene terephthalate film substrate on which a temperature-responsive polymer layer and an adhesive layer are provided, with the adhesive layer being protected with a detachable film (i.e., the cell support film 810 shown in FIG. 8), was produced.

B. Processing of Temperature-Responsive Cell Support Film

A long-sized, temperature-responsive cell support film was cut into square pieces (7.5 cm×7.5 cm) using a laser beam machine, and it was then separated into individual sheets.

C. Mounting of Temperature-Responsive Cell Support Film

A polystyrene flask component (Nunc) comprising a dish-like bottom plate member provided with a through-hole (i.e., the first member 401 shown in FIG. 4) and a top plate member mounted on the bottom plate member (i.e., the second member 402 shown in FIG. 4) was provided. The detachable film was removed from the separated temperature-responsive cell support film, the surface coated with an adhesive was allowed to adhere to the inner surface of the bottom plate member, and the temperature-responsive cell support film was integrated with the bottom plate member.

D. Assembly of Flask Housing

While the top plate member was joined with the bottom plate member, these two members were welded to each other at the sites of contact using ultrasonic welding equipment, and a flask-type container section was thus assembled.

E. Confirmation of Temperature Responsiveness

Bovine aortic endothelial cells were prepared to adjust the surface cell density to $6.25 \times 10^3$ cells/cm$^2$ and seeded in an inner chamber of the prepared flask-type container section. DMEM containing 10% FBS (Sigma) was used, and culture was conducted in a $CO_2$ incubator at 37° C. in the presence of 5% $CO_2$ for 20 hours. Thereafter, the flask was introduced into an incubator at 20° C. in the presence of 5% $CO_2$. The flask was removed from the incubator at 20° C. 30 minutes later. Detachment of cells that had adhered to the surface of the temperature-responsive cell support film on which culture had been conducted was verified.

Example 2

Adhesion with the Use of Adhesive and Defoaming

Subsequently, a detachable film was removed from the sheet-like temperature-responsive cell support film, the surface coated with an adhesive was allowed to adhere to the inner surface of the bottom plate member, the temperature-responsive cell support film was integrated with the bottom plate member, and the resultant was subjected to defoaming in an autoclave at a pressure of 0.4 MPa and a temperature of 40° C. for 30 minutes. The temperature-responsive cell support film was visually inspected to confirm the complete absence of foams between the film and the bottom plate member. Culture was conducted under the same conditions as in Example 1, and it was confirmed that the cells that had adhered to the surface of the temperature-responsive cell support film could be detached.

Example 3

Sterilization by 5 KGy of γ Rays

The through-hole portion of the flask-type container section produced in Example 1 was stoppered to hermetically seal the flask, and the flask was vacuum packaged in a transparent film. The flask was irradiated with 5 kGy of γ rays in such state for sterilization. Culture was conducted in the sterilized flask under the same conditions as in Example 1, and it was confirmed that cells that had formed on the surface of the temperature-responsive cell support film on which culture had been conducted could be detached.

Example 4

Sterilization by 10 kGy of γ Rays

Cells were detached through substantially the same treatment as in Example 3, except that the energy of γ rays to be applied was changed to 10 kGy. It was confirmed that cells that had formed on the surface of the temperature-responsive cell support film on which culture had been conducted could be detached.

Reference Example 1

The through-hole portion of the flask produced in Example 1 was stoppered to hermetically seal the flask, and the flask was irradiated with 5 kGy of γ rays in the air. Culture was conducted in the sterilized flask under the same conditions as in Example 1. As a result, it was confirmed that the cell sheet that had formed on the surface of the temperature-responsive cell support film on which culture had been conducted could be detached, although the detachability was poorer than that attained in Examples 3 and 4.

Reference Example 2

The through-hole portion of the flask produced in Example 1 was stoppered to hermetically seal the flask, and the flask was irradiated with 10 kGy of γ rays in the air. Culture was conducted in the sterilized flask under the same conditions as in Example 1. As a result, it was confirmed that the cell sheet that had formed on the surface of the temperature-responsive cell support film on which culture had been conducted could be detached, although the detachability was poorer than that attained in Examples 3 and 4.

Reference Example 3

The through-hole portion of the flask produced in Example 1 was stoppered to hermetically seal the flask, the flask was irradiated with ultraviolet rays for sterilization, and the cell peeling test was conducted in the same manner. In Examples 3 and 4 in which sterilization by γ ray application was carried out in vacuo, the destroyed organism species exhibited cell detachability equivalent to that attained by limited ultraviolet application.

Reference Example 4

The cell peeling test was conducted in the same manner, except for the use of a commercialized cell culture vessel provided with a temperature-responsive polymer. In Examples 3 and 4 in which sterilization by γ ray application was carried out in vacuo, cell detachability equivalent to that attained by limited ultraviolet application was observed.
(Cell Peeling Test)

Cell detachability observed in Examples 3 and 4 and Reference Examples 1 to 4 was examined in accordance with the method described in JP Patent Publication No. 2009-82123 A.

Figure 19:
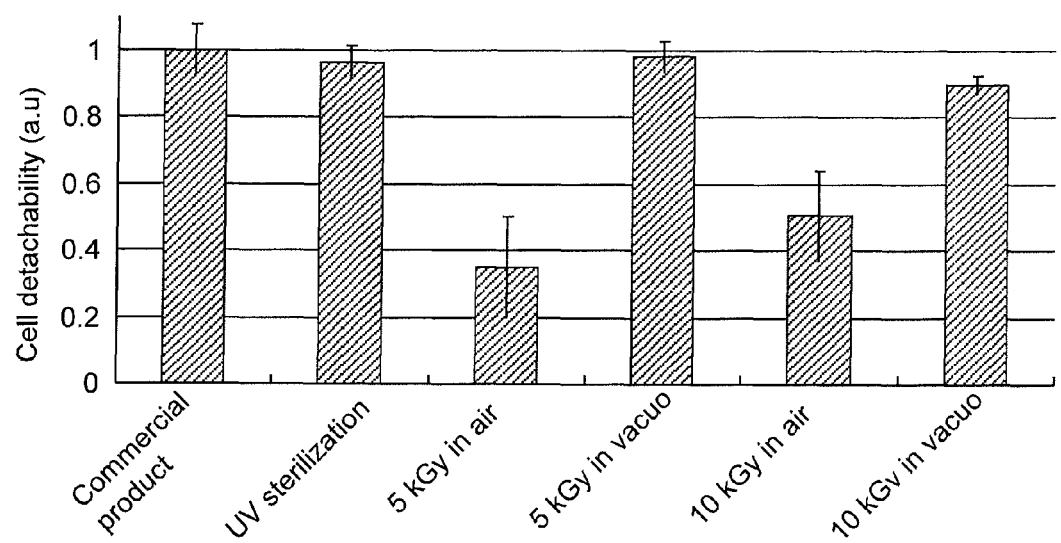
FIG. 19 shows the correlation between a sterilization means and cell peeling performance.

FIG. 19 shows cell detachability relative to the level of cell detachability designated as 1.0, which was observed in Reference Example 4 (a commercial product).

Example 5

Ultrasonic Welding

The temperature-responsive cell support film was directly set on a dish-like bottom plate member (i.e., the first member 401' shown in FIG. 15), and the support film was integrated with the bottom plate member by ultrasonic welding. An ultrasonic generator of ultrasonic welding equipment was applied to the temperature-responsive cell support film along the periphery thereof to allow the temperature-responsive cell support film to be welded to the bottom plate member. Subsequently, the top plate member was bonded to the bottom plate member using ultrasonic welding equipment to assemble the flask. Culture was conducted using this flask under the same conditions as in Example 1. As a result, it was confirmed that a cell sheet that had formed on the surface of the temperature-responsive cell support film on which culture had been conducted could be detached.

Example 6

In-Mold Forming

As a molding apparatus, α-100C (Fanuc Corporation) was used. A core mold and a cavity mold for constituting a cavity in the form of a flask top plate were prepared. After the temperature-responsive cell support film had been disposed in the core mold, the core mold was joined with the cavity mold, and molten polystyrene was then fed into the cavity. Molding was carried out at a resin temperature of 220° C. and a mold temperature of 20° C. Thereafter, the temperature-responsive cell support film integrated with the top plate was removed, and the top plate was bonded to a dish-like bottom plate member provided with a through-hole using ultrasonic welding equipment to assemble the flask. Culture was conducted using the resulting flask under the same conditions as in Example 1, and it was confirmed that a cell sheet that had formed on the surface of the temperature-responsive cell support film could be detached.

Example 7

Adhesion with the Use of Adhesive

A flask-type culture vessel was produced in the same manner as described in the section "A. Production of temperature-responsive cell support film" of Example 1, except that the features described below were modified. It was confirmed that the resulting flask-type culture vessel had cell sheet detachability equivalent to that of the culture vessel of Example 1.

A full roll of an easy-adhesion polyethylene terephthalate film in the form of a 17-cm-wide band was prepared. The film was fed out of the full roll, the coating solution as used in Example 1 was applied to the film surface by gravure coating, and the coated film was dried by being passed through a hot-air drier at 40° C. for 10 seconds. The coated film was irradiated with electron beams to graft-polymerize N-isopropylacrylamide, poly-N-isopropylacrylamide was fixed to the film surface, and a temperature-responsive polymer layer was formed on the surface of the polyethylene terephthalate film substrate.

Separately, a full roll of a detachable film in the form of a 17-cm-wide band was prepared. As a coating solution for forming an adhesive, an acrylic polymer, SK Dyne 2147 (Soken Chemical & Engineering Co., Ltd.), was prepared. The detachable film was fed out of the full roll, the coating solution for forming an adhesive was applied to the surface of the detachable film using a comma coater, the coated film was treated at 90° C. for 2 minutes, and an adhesive layer was thus formed on the surface of the detachable film.

The long-sized detachable film provided with the resulting adhesive layer was allowed to adhere to the long-sized polyethylene terephthalate film substrate provided with the temperature-responsive polymer in such a manner that the adhesive layer was brought into contact with the film substrate layer, and the resultant was then rewound as a roll. Thus, the long-sized cell support film comprising a polyethylene terephthalate film substrate wound as a roll and a temperature-responsive polymer and an adhesive layer provided on the surface thereof, with the adhesive layer being protected by the detachable film, was prepared (i.e., the cell support film 810 shown in FIG. 8).

DESCRIPTION OF NUMERAL REFERENCES

100 and 200: Container sections
120 and 220: Cell culture vessels
130: Inner chamber
140, 610, 810, and 910: Cell support films
401 and 501: First members
402, 502, and 503: Other members All publications, patents, and patent applications cited herein are incorporated herein by reference in their entirety.

We claim:
1. A method for producing a cell culture vessel comprising a container section in which an inner chamber for accom- modating cells and media is provided, the container section comprising a cell support film, which is at least provided with a film substrate layer and, disposed thereon, a stimuli-responsive polymer layer having a cell-adhesive surface capable of changing into a non-cell-adhesive surface upon reception of a particular stimulus, fixed to at least a part of the inner wall surface facing the inner chamber in a manner such that the stimuli-responsive polymer layer is disposed facing the inner chamber, the method comprising:
- a step of cutting a long-sized cell support film to prepare a sheet-like cell support film;
- a step of cell support film fixation comprising fixing a sheet-like cell support film to a first member of the container section having a region of an opened inner wall surface to which the cell support film is fixed, thereby producing a film-fixed first member;
- a step of member bonding for constituting the container section by bonding the film-fixed first member to one or more other members; and
- a step of sterilization by irradiation of the cell culture vessel with a γ beam under vacuum conditions.

2. The method according to claim 1, further comprising a step of producing a long-sized cell support film, wherein the step of producing a long-sized cell support film comprises unwinding the rolled long-sized film substrate to feed the unwound film substrate, forming a stimuli-responsive polymer layer on the unwound film substrate, and rewinding the formed film substrate as a roll.

3. The method according to claim 1, wherein the step of cutting comprises cutting the long-sized cell support film to prepare a polygonal sheet-like cell support film.

4. The method according to claim 1, wherein the step of cell support film fixation comprises a step of allowing the sheet-like cell support film to adhere to the first member with the aid of an adhesive.

5. The method according to claim 1, wherein the step of cell support film fixation comprises a step of fixing the sheet-like cell support film to the first member by heat sealing.

6. The method according to claim 1, wherein the step of cell support film fixation comprises a step of fixing the sheet-like cell support film to the first member by ultrasonic welding.

7. The method according to claim 1, wherein the step of cell support film fixation comprises a step of fixing the sheet-like cell support film to the first member by laser-beam welding.

8. The method according to claim 1, wherein the step of cell support film fixation comprises a step of introducing resin into an injection mold in which the sheet-like cell support film is disposed in advance to prepare the first member and obtaining the film-fixed first member.

9. The method according to claim 1, wherein the step of cell support film fixation comprises a step of introducing resin into an injection mold in which the sheet-like cell support film is disposed in advance to prepare the first member and obtaining the film-fixed first member, the cell support film further comprising a heat-sealable resin layer formed on a surface of the film substrate layer opposite from the stimuli-responsive polymer layer.

10. The method according to claim 1, wherein the step of cell support film fixation comprises a step of fixing the sheet-like cell support film to the first member with the use of a physical locking means.

* * * * *